(12) United States Patent
Quigley et al.

(10) Patent No.: US 11,883,864 B2
(45) Date of Patent: Jan. 30, 2024

(54) AUTOMATED COMPLIANCE MEASUREMENT AND CONTROL FOR LANDFILL GAS EXTRACTION SYSTEMS

(71) Applicant: Loci Controls, Inc., Wareham, MA (US)

(72) Inventors: Peter Quigley, Duxbury, MA (US); Ian Martin, Higganum, CT (US); Jack Rowbottom, Swansea, MA (US); Nicole Neff, North Potomac, MD (US)

(73) Assignee: Loci Controls, Inc., Wareham, MA (US)

( * ) Notice: Subject to any disclaimer, the term of this patent is extended or adjusted under 35 U.S.C. 154(b) by 0 days.

(21) Appl. No.: 17/152,252

(22) Filed: Jan. 19, 2021

(65) Prior Publication Data

US 2021/0229142 A1    Jul. 29, 2021

Related U.S. Application Data

(60) Provisional application No. 62/967,147, filed on Jan. 29, 2020.

(51) Int. Cl.
 *B09B 1/00* (2006.01)
(52) U.S. Cl.
 CPC .................................... *B09B 1/006* (2013.01)
(58) Field of Classification Search
 CPC ..................................................... B09B 1/006
 See application file for complete search history.

(56) References Cited

U.S. PATENT DOCUMENTS 3,062,037 A    11/1962  Donner et al.
3,567,387 A     3/1971  Jones
(Continued)

FOREIGN PATENT DOCUMENTS

EP        0 743 515 A1   11/1996
WO    WO 2006/005014 A2    1/2006
(Continued)

OTHER PUBLICATIONS

Automated Landfill Gas Collection Increases Landfill Gas Flow and Quality at Oklahoma City Landfill Bingham, et al. undated. Accessed Aug. 2022. (Year: 2022).*
(Continued)

*Primary Examiner* — Janine M Kreck
(74) *Attorney, Agent, or Firm* — Wolf, Greenfield & Sacks, P.C.

(57) ABSTRACT

A method for use by a system coupled to at least one sensor and at least one flow control mechanism of a gas extraction system, the system comprising at least one controller and configured for use in connection with a landfill gas extraction process for extraction of landfill gas from a landfill via the gas extraction system, the method comprising: using the at least one controller to perform: obtaining, based on at least one measurement made by the at least one sensor, at least one current value indicative of a selected characteristic of the landfill gas extraction process, determining, at discrete time intervals, whether the at least one current value satisfies at least one compliance criterion for the selected characteristic, and when it is determined that the at least one current value does not satisfy the at least one compliance criterion for the selected characteristic, performing a corrective action.

14 Claims, 17 Drawing Sheets

(56) References Cited

U.S. PATENT DOCUMENTS

| | | |
|---|---|---|
| 4,026,355 A | 5/1977 | Johnson et al. |
| 4,191,541 A | 3/1980 | Jenkins |
| 4,226,675 A | 10/1980 | Lewis et al. |
| 4,227,897 A | 10/1980 | Reed |
| 4,494,380 A | 1/1985 | Cross |
| 4,499,378 A | 2/1985 | Miyatake et al. |
| 4,670,148 A | 6/1987 | Schneider |
| 4,890,672 A | 1/1990 | Hall |
| 5,063,519 A | 11/1991 | Zison |
| 5,209,941 A | 5/1993 | Wuest |
| 5,223,229 A | 6/1993 | Brucker |
| 5,239,861 A | 8/1993 | Fujita et al. |
| 5,451,249 A | 9/1995 | Spiegel et al. |
| 5,458,006 A | 10/1995 | Roqueta |
| 5,665,314 A | 9/1997 | Berger et al. |
| 5,681,360 A | 10/1997 | Siwajek et al. |
| 5,695,641 A | 12/1997 | Cosulich et al. |
| 5,830,262 A | 11/1998 | Marchini et al. |
| 6,169,962 B1 | 1/2001 | Brookshire et al. |
| 6,196,324 B1 | 3/2001 | Giacomino et al. |
| 6,231,153 B1 | 5/2001 | Elgee |
| 6,241,950 B1 | 6/2001 | Veelenturf et al. |
| 6,399,391 B1 | 6/2002 | Tomlin |
| 6,497,804 B1 | 12/2002 | Gorfinkel et al. |
| 6,591,695 B1 | 7/2003 | Brookshire et al. |
| 6,595,287 B2 | 7/2003 | Fisher |
| 6,611,760 B2 | 8/2003 | Bentley et al. |
| 6,749,368 B2 | 6/2004 | Ankeny et al. |
| 6,799,477 B2 | 10/2004 | Brookshire et al. |
| 6,999,883 B1 | 2/2006 | Brady et al. |
| 7,187,299 B2 | 3/2007 | Kunerth et al. |
| 7,198,433 B2 | 4/2007 | Augenstein et al. |
| 7,243,730 B2 | 7/2007 | Casey |
| 7,273,098 B2 | 9/2007 | Evans et al. |
| 7,373,976 B2 | 5/2008 | Casey |
| 7,387,163 B2 | 6/2008 | Seegers et al. |
| 7,448,828 B2 | 11/2008 | Augenstein et al. |
| 7,748,450 B2 | 7/2010 | Mundell |
| 7,866,921 B2 | 1/2011 | Stamoulis |
| 7,950,464 B2 | 5/2011 | Atencio et al. |
| 7,972,082 B2 | 7/2011 | Augenstein et al. |
| 8,047,276 B2 | 11/2011 | Stamoulis |
| 8,163,242 B2 | 4/2012 | Elkins |
| 8,168,121 B2 | 5/2012 | Elkins |
| 8,186,211 B2 | 5/2012 | Boult et al. |
| 8,840,708 B1 | 9/2014 | Morrow et al. |
| 8,924,029 B2 | 12/2014 | Nath et al. |
| 8,927,909 B2 | 1/2015 | Le Neel et al. |
| 8,944,014 B2 | 2/2015 | Cutlip et al. |
| 9,062,536 B2 | 6/2015 | Fischer et al. |
| 10,029,290 B2 | 7/2018 | Campanella et al. |
| 10,042,402 B2 | 8/2018 | Eremenko et al. |
| 10,400,560 B2 | 9/2019 | Campanella et al. |
| 10,408,747 B2 | 9/2019 | Schlueter et al. |
| 10,449,578 B2 | 10/2019 | Campanella et al. |
| 10,556,259 B2 | 2/2020 | Campanella et al. |
| 10,576,514 B2 | 3/2020 | Campanella et al. |
| 10,576,515 B2 | 3/2020 | Campanella et al. |
| 10,639,687 B2 | 5/2020 | Campanella et al. |
| 10,682,678 B2 | 6/2020 | Campanella et al. |
| 10,705,063 B2 | 7/2020 | Campanella et al. |
| 10,882,086 B2 | 1/2021 | Quigley et al. |
| 10,946,420 B2 | 3/2021 | Quigley et al. |
| 11,007,555 B2 | 5/2021 | Campanella et al. |
| 11,067,549 B2 | 7/2021 | Campanella et al. |
| 11,072,006 B2 | 7/2021 | Campanella et al. |
| 11,084,074 B2 | 8/2021 | Campanella et al. |
| 11,235,361 B2 | 2/2022 | Quigley et al. |
| 11,273,473 B2 | 3/2022 | Quigley et al. |
| 11,484,919 B2 | 11/2022 | Quigley et al. |
| 11,491,521 B2 | 11/2022 | Quigley et al. |
| 11,602,777 B2 | 3/2023 | Campanella et al. |
| 11,602,778 B2 | 3/2023 | Campanella et al. |
| 2001/0005812 A1 | 6/2001 | Brookshire et al. |
| 2002/0101718 A1 | 8/2002 | Negishi |
| 2003/0000281 A1 | 1/2003 | Ketler et al. |
| 2003/0046975 A1 | 3/2003 | Wewers et al. |
| 2004/0055359 A1 | 3/2004 | Ketler et al. |
| 2004/0121201 A1 | 6/2004 | Roche et al. |
| 2006/0034664 A1 | 2/2006 | Augenstein et al. |
| 2006/0251540 A1 | 11/2006 | Benning et al. |
| 2007/0224085 A1 | 9/2007 | Tooley |
| 2007/0225923 A1 | 9/2007 | Tooley |
| 2007/0254196 A1 | 11/2007 | Richards et al. |
| 2008/0011248 A1 | 1/2008 | Cutlip et al. |
| 2008/0127726 A1 | 6/2008 | Elkins |
| 2009/0136298 A1 | 5/2009 | Augenstein et al. |
| 2010/0310733 A1 | 12/2010 | Hoffman |
| 2011/0061439 A1 | 3/2011 | Dong et al. |
| 2011/0061874 A1 | 3/2011 | Stamoulis |
| 2011/0081586 A1 | 4/2011 | McAlister |
| 2011/0132104 A1 | 6/2011 | Benson et al. |
| 2011/0198094 A1 | 8/2011 | Stamoulis |
| 2011/0231099 A1 | 9/2011 | Elkins |
| 2011/0272420 A1 | 11/2011 | Landess et al. |
| 2012/0191349 A1 | 7/2012 | Lenz et al. |
| 2012/0206715 A1 | 8/2012 | Laub |
| 2012/0287418 A1 | 11/2012 | Scherer et al. |
| 2013/0036811 A1 | 2/2013 | Boult |
| 2013/0180703 A1 | 7/2013 | Colby |
| 2013/0193325 A1 | 8/2013 | Phillips et al. |
| 2013/0247647 A1 | 9/2013 | Mahoney et al. |
| 2013/0334418 A1 | 12/2013 | Cowie et al. |
| 2014/0023576 A1 | 1/2014 | Yezerets et al. |
| 2014/0182846 A1 | 7/2014 | Fischer et al. |
| 2014/0284935 A1 | 9/2014 | Disbennett et al. |
| 2014/0338878 A1 | 11/2014 | Tessnow |
| 2015/0000426 A1 | 1/2015 | Mustang |
| 2015/0168274 A1 | 6/2015 | Sheffield |
| 2015/0226045 A1 | 8/2015 | Fischer et al. |
| 2015/0275632 A1 | 10/2015 | Fischer et al. |
| 2015/0330938 A1 | 11/2015 | Henson et al. |
| 2015/0354032 A1 | 12/2015 | Yuan et al. |
| 2015/0362468 A1 | 12/2015 | Gerhold |
| 2016/0011159 A1 | 1/2016 | Sekiya et al. |
| 2016/0025365 A1 | 1/2016 | Moudy |
| 2016/0025696 A1 | 1/2016 | Birks et al. |
| 2016/0033391 A1 | 2/2016 | Stroganov et al. |
| 2016/0123946 A1 | 5/2016 | Dufresne |
| 2016/0169826 A1 | 6/2016 | Youssi et al. |
| 2016/0209133 A1 | 7/2016 | Hu et al. |
| 2016/0237007 A1 | 8/2016 | Morrow et al. |
| 2016/0238494 A1 | 8/2016 | Chrin, II |
| 2016/0247183 A1 | 8/2016 | Foody |
| 2016/0287870 A1 | 10/2016 | Yip et al. |
| 2016/0377457 A1 | 12/2016 | Zhang et al. |
| 2017/0080762 A1 | 3/2017 | Guinart et al. |
| 2017/0122065 A1 | 5/2017 | Fischer et al. |
| 2017/0173505 A1 | 6/2017 | Dhingra et al. |
| 2017/0176590 A1 | 6/2017 | Sharonov et al. |
| 2017/0216891 A1 | 8/2017 | Campanella et al. |
| 2017/0216892 A1 | 8/2017 | Campanella et al. |
| 2017/0216893 A1* | 8/2017 | Campanella ............ B09B 1/00 |
| 2017/0218730 A1 | 8/2017 | Campanella et al. |
| 2017/0218731 A1 | 8/2017 | Campanella et al. |
| 2017/0218732 A1 | 8/2017 | Campanella et al. |
| 2017/0254196 A1 | 9/2017 | Campanella et al. |
| 2017/0254787 A1 | 9/2017 | Campanella et al. |
| 2017/0328750 A1 | 11/2017 | Jehle et al. |
| 2018/0003572 A1 | 1/2018 | Garsd et al. |
| 2018/0003684 A1 | 1/2018 | Kerr |
| 2018/0024202 A1 | 1/2018 | Erickson et al. |
| 2018/0154408 A1 | 6/2018 | Ko et al. |
| 2018/0164137 A1 | 6/2018 | Layher et al. |
| 2018/0171604 A1 | 6/2018 | Kim et al. |
| 2018/0209248 A1 | 7/2018 | Patel et al. |
| 2018/0304323 A1 | 10/2018 | Campanella et al. |
| 2019/0069245 A1 | 2/2019 | Miller et al. |
| 2019/0232346 A1 | 8/2019 | Speer et al. |
| 2019/0277119 A1 | 9/2019 | Campion |
| 2019/0277821 A1 | 9/2019 | Quigley et al. |
| 2020/0086365 A1 | 3/2020 | Campanella et al. |
| 2020/0101504 A1 | 4/2020 | Quigley et al. |
| 2020/0101505 A1 | 4/2020 | Quigley et al. |

(56) References Cited

U.S. PATENT DOCUMENTS

| | | |
|---|---|---|
| 2020/0130033 A1 | 4/2020 | Campanella et al. |
| 2020/0197990 A1 | 6/2020 | Quigley et al. |
| 2020/0254497 A1 | 8/2020 | Campanella et al. |
| 2020/0306806 A1 | 10/2020 | Quigley et al. |
| 2020/0306807 A1 | 10/2020 | Quigley et al. |
| 2021/0046524 A1 | 2/2021 | Quigley et al. |
| 2021/0178436 A1 | 6/2021 | Quigley et al. |
| 2021/0372977 A1 | 12/2021 | Campanella et al. |
| 2022/0008970 A1 | 1/2022 | Quigley et al. |
| 2022/0008971 A1 | 1/2022 | Quigley et al. |
| 2022/0008972 A1 | 1/2022 | Quigley et al. |
| 2022/0008973 A1 | 1/2022 | Quigley et al. |
| 2022/0062959 A1 | 3/2022 | Campanella et al. |
| 2022/0062960 A1 | 3/2022 | Campanella et al. |

FOREIGN PATENT DOCUMENTS

| | | |
|---|---|---|
| WO | WO 2015/072989 A1 | 5/2015 |
| WO | WO 2016/010985 A1 | 1/2016 |
| WO | WO 2018/194650 A1 | 10/2018 |
| WO | WO 2020/072457 A1 | 4/2020 |

OTHER PUBLICATIONS

U.S. Appl. No. 14/532,807, Campanella et al., †Nov. 4, 2014.
U.S. Appl. No. 15/456,936, Campanella et al., †Mar. 13, 2017.
U.S. Appl. No. 15/456,982, Campanella et al., †Mar. 13, 2017.
U.S. Appl. No. 15/464,236, Campanella et al., †Mar. 20, 2017.
U.S. Appl. No. 15/478,583, Campanella et al., †Apr. 4, 2017.
U.S. Appl. No. 15/493,174, Campanella et al., †Apr. 21, 2017.
U.S. Appl. No. 15/493,184, Campanella et al., †Apr. 21, 2017.
U.S. Appl. No. 15/493,201, Campanella et al., †Apr. 21, 2017.
U.S. Appl. No. 16/024,085, Campanella et al., †Jun. 29, 2018.
U.S. Appl. No. 16/290,387, Quigley et al., †Mar. 2, 2019.
U.S. Appl. No. 16/589,372, Quigley et al., †Oct. 1, 2019.
U.S. Appl. No. 16/589,391, Quigley et al., †Oct. 1, 2019.
U.S. Appl. No. 16/694,745, Campanella et al., †Nov. 25, 2019.
U.S. Appl. No. 16/726,232, Campanella et al., †Dec. 23, 2019.
U.S. Appl. No. 16/745,892, Campanella et al., †Jan. 17, 2020.
U.S. Appl. No. 16/831,131, Campanella et al., †Mar. 26, 2020.
U.S. Appl. No. 16/901,405, Quigley et al., †Jun. 15, 2020.
U.S. Appl. No. 16/901,430, Quigley et al., †Jun. 15, 2020.
U.S. Appl. No. 16/927,471, Quigley et al., †Jul. 13, 2020.
U.S. Appl. No. 16/927,479, Quigley et al., †Jul. 13, 2020.
U.S. Appl. No. 16/927,482, Quigley et al., †Jul. 13, 2020.
U.S. Appl. No. 16/927,488, Quigley et al., †Jul. 13, 2020.
U.S. Appl. No. 17/086,987, Quigley et al., †Nov. 2, 2020.
U.S. Appl. No. 17/167,539, Quigley et al., †Feb. 4, 2021.
Extended European Search Report for European Application No. 17760717.3 dated Oct. 2, 2019.
Extended European Search Report for European Application No. 17906368.0 dated Oct. 15, 2020.
International Search Report and Written Opinion for International Application No. PCT/US2017/020196 dated Jun. 7, 2017.
International Search Report and Written Opinion for International Application No. PCT/US17/28818 dated Sep. 8, 2017.
International Search Report and Written Opinion for International Application No. PCT/US2019/020251 dated May 31, 2019.
International Search Report and Written Opinion for International Application No. PCT/US2019/054013 dated Dec. 4, 2019.
Invitation to Pay Additional Fees for International Application No. PCT/US17/28818 dated Jul. 10, 2017.
[No Author Listed], 50% CH4, 35% CO2, 15% N2. Instrument Depot. 2015. http://www.instrumentdepot.com/50-methane-35-carbon-dioxide-15-nitrogen-c-1_27_472.html [last accessed Sep. 25, 2015].
[No Author Listed], Cloud-Based Wellwatcher Analytics Platform Offers 24/7/365 Visibility on Landfill Gas-Collection Systems. Tech Note. Loci Controls. Nov. 2016. 1 page.
[No Author Listed], Increase Landfill Gas Collection by up to 30%. Tech Note. Loci Controls. Oct. 2016. 1 page.
[No Author Listed], Loci Controller Combines Active Flow Control With 24/7/365 Real-Time Gas-Composition Analysis to Maximize Landfill Gas Extraction. Tech Note. Loci Controls. Nov. 2016. 1 page.
[No Author Listed], Loci Sentry Utilizes Passive Flow and Gas-Composition Monitoring in Conjunction With Loci Controller and Wellwatcher Analytics to Maximize Landfill Gas Collection. Tech Note. Loci Controls. Nov. 2016. 1 page.
[No Author Listed], Methacontrol® Optimizing landfill gas recovery. Oct. 9, 2013. http://www.veolia.com/en/veolia-group/media/news/methacontrol-r. 1 page.
Bieker et al., Real-Time Production Optimization of Offshore Oil and Gas Production Systems: A Technology Survey. SPE International. 2006. 8 pages.
Collins et al., Web-based monitoring of year-length deployments of autonomous gas sensing platforms on landfill sites. 2011 IEEE Sensors Proceedings. 2011:1620-3.
Fay et al., Remote Real-Time Monitoring of Subsurface Landfill Gas Migration. Sensors. 2011;11(7):6603-29.
Xu et al., Impact of changes in barometric pressure on landfill methane emission. AGU Publications. Jul. 10, 2014. 17 pages.
U.S. Appl. No. 17/343,317, Campanella et al., †Jun. 9, 2021.
U.S. Appl. No. 17/369,395, Campanella et al., †Jul. 7, 2021.
U.S. Appl. No. 17/369,318, Campanella et al., Jul. 7, 2021.
International Search Report and Written Opinion for International Application No. PCT/US2021/013850 dated Jun. 21, 2021.
International Search Report and Written Opinion for International Application No. PCT/US2021/040653 dated Nov. 26, 2021.
Communication pursuant to Article 94(3) EPC for European Application No. 17760717.3 dated Feb. 21, 2022.
U.S. Appl. No. 17/959,446, Quigley et al., †Oct. 4, 2022.
[No Author Listed], Green House Gas Emissions Reduction with Loci Controls. YouTube. Jun. 25, 2021. https://www.youtube.com/watch?v=- reQosq7TJw&t=50s [last accessed Nov. 10, 2022]. 3 pages.
[No Author Listed], Loci—EPP RNG Works Presentation Preview. YouTube. Sep. 5, 2019. https://www.youtube.com/watch?v=33_WcvJxidY&t=128s [last accessed Nov. 10, 2022]. 3 pages.
[No Author Listed], Loci Controls—Automated Landfill Wellfield Tuning to External Variables. YouTube. Mar. 5, 2021. https://www.youtube.com/watch?v=AdQRep0x3XM&t=82s [last accessed Nov. 10, 2022]. 4 pages.
[No Author Listed], Loci Controls—Automated Wellfield Tuning. YouTube. Mar. 5, 2021. https://www.youtube.com/watch?v=IbdMx2CCKbc&t=100s [last accessed Nov. 10, 2022]. 5 pages.
[No Author Listed], Loci Controls, Inc Expands Number of Proprietary Advanced Technologies, Company Adds Flo-Wing Meter Measurement System to Its Roster of Issued Patents. News Release. Apr. 6, 2021. https://www.locicontrols.com/perch/resources/loci-expands-advanced-technologies-with-flo-wing-1.pdf [Last accessed Nov. 10, 2022]. 2 pages.
[No Author Listed], Loci Controls, Inc. Achieves Milestone with Exceptional Safety Record. News Release. Oct. 20, 2021. https://www.locicontrols.com/perch/resources/loci-achieves-exceptional-safety-record-1.pdf [Last accessed Nov. 10, 2022]. 2 pages.
[No Author Listed], Loci Controls, Inc. and American Carbon Registry Develop New Carbon Market Incentives to Reduce Methane Emissions from Large Landfills. News Release. 3. Jun. 2021. https://www.locicontrols.com/perch/resources/acr-approves-loci-methodology-1.pdf [Last accessed Nov. 10, 2022]. 3 pages.
Messics et al., Automated Landfill Gas Collection Improves Operations and Increases Revenue for one of the Largest High-BTU Landfill-Gas-to-Energy Sites in the US. Technical Paper. Sep. 10, 2019. 10 pages.
Office Communication dated May 12, 2022 for U.S. Appl. No. 16/927,479.
Office Communication dated May 3, 2022 for U.S. Appl. No. 16/927,471.
Response to Office Action filed Nov. 2, 2022 for U.S. Appl. No. 16/927,471.

(56) References Cited

OTHER PUBLICATIONS

Response to Office Action filed Nov. 2, 2022 for U.S. Appl. No. 16/927,479.
Extended European Search Report for European Application No. 19869105.7 dated May 23, 2022.
Communication pursuant to Article 94(3) EPC for European Application No. 17906368.0 dated Aug. 4, 2022.
International Preliminary Report on Patentability for International Application No. PCT/US2019/054013 dated Apr. 15, 2021.
International Preliminary Report on Patentability for International Application No. PCT/US2021/013850 dated Aug. 11, 2022.
Caton et al., Automated Landfill Gas Collection Increases Uptime and Revenue for Landfill in Lawrence, KS. Loci Controls. 2019. 22 pages. [Last accessed May 11, 2022].
Quigley, Loci Controls, Inc. (Fall River, MA), and Enerdyne Power Systems Inc., ("Enerdyne", Charlotte, NC). Loci Controls. Aug. 2019. 2 pages. [Last accessed May 11, 2022].
U.S. Appl. No. 18/158,742, Campanella et al., †Jan. 24, 2023.
U.S. Appl. No. 18/168,983, Campanella et al., †Feb. 14, 2023.
International Preliminary Report on Patentability for International Application No. PCT/US2021/040653 dated Jan. 26, 2023.
[No Author Listed], For Immediate Release: Loci Controls announces enhancements for 2018 to automated landfill gas collection products and services. May 2020. 2 pages. www.locicontrols.com (Last accessed Jan. 2023).

* cited by examiner

1100

Calibration Record

| Loci Model | Controller |
|---|---|
| Loci Unit # | 001601 |
| Well or Header ID # | L81DBC4 |
| Date: | 11/28/2019 |
| Time: | 09:35 |

— 1101

Gas Composition Calibration — 1102

| | CH₄% | CO₂% | O₂% | N₂% | Batch ID |
|---|---|---|---|---|---|
| Calibration Fluid #1 | 0.0 | 0.0 | 20.9 | 78.1 | Air |
| Calibration Fluid #2 | 50.0 | 35.0 | 0.0 | 15.0 | -- |
| Reading Before Calibration | 50.6 | 34.4 | 0.0 | 15.0 | |
| Confirmation Reading | 50.1 | 34.8 | 0.0 | 15.1 | |

| Pass/Fail | Pass |
|---|---|

— 1104

| | Date | Time | Temp Before Calibration (°F) | Temp After Calibration (°F) |
|---|---|---|---|---|
| Thermistor Calibration | -- | -- | 0.0 | 0.0 |
| | Make | Model | Calibration Date | |
| Temperature Calibration Instrument | | | -- | |

— 1106

| | Date | Time | Pressure Before Calibration (°H₂O) | Pressure After Calibration (°H₂O) |
|---|---|---|---|---|
| Pressure Sensor Calibration | 11/20/2019 | 12:46 | -3.9 | 0.0 |
| Calibration Medium | Atmosphere | | | |

Loci Automated Gas Collection - Site Health

| Alarm | Collector | Value |
|---|---|---|
| Calibration Error | OL81DBC2 | 10 failures |
| Calibration Error | OL81DTC1 | 1 failure |
| Communication Loss | OL81DBC2 | 22 hours late |
| Red Flag: Pressure | OLGW6845 | 0.4 H₂0 |
| Yellow Flag: Temperature | OLGW6845 | 139.5 °F |

Showing 1 to 5 of 5 entries

Dashboard
Site Info
Map View
Table View
Collector Details
Collector Settings
Site Health
Automation
Reports
Compliance/Alerts
User Settings Active Collectors: 10
Total CH₄ Flow: 118 SCFM
Total LFG Flow: 216 SCFM
Total CO₂: 38.4%
Total CH₄: 58.5%

Sign Out

Loci Automated Gas Collection - Table View
1704

| Collector ≑ | CH4 (%) ≑ | O2 (%) ≑ | CO2 (%) ≑ | Bal. Gas (%) ≑ | LFG Flow (SCFM) ≑ | Temperature (F) ≑ | PA (in. H2O) ≑ | PB (in. H2O) ≑ | Valve Position (%) ≑ |
|---|---|---|---|---|---|---|---|---|---|
| OL810B02 | 48.4 | 1.0 | 35.7 | 14.9 | 10.7 | 98.9 | -8.9 | -50.0 | 10.2 |
| OL810B04 | 55.0 | 0.0 | 40.8 | 3.3 | 16.7 | 98.6 | -10.6 | -48.1 | 15.0 |
| OL810B02 | 59.5 | 0.2 | 37.9 | 3.3 | 33.2 | 96.7 | -0.4 | -45.7 | 27.9 |
| OL810B01 | 57.5 | 0.1 | 38.8 | 2.5 | 41.6 | 104.0 | -0.9 | -42.0 | 30.6 |
| OL810B01 | 55.9 | 1.7 | 35.0 | 7.2 | 18.4 | 96.1 | -0.9 | -45.4 | 22.5 |
| OL810B06 | 57.2 | 0.3 | 39.8 | 2.8 | 29.5 | 142.6 | -10.4 | -37.3 | 32.2 |
| OL810B07 | 59.9 | 0.1 | 35.5 | 4.4 | 0.0 | 94.5 | -3.1 | -21.0 | 32.9 |
| OL810B07 | 53.0 | 2.5 | 37.1 | 7.5 | 29.6 | 105.4 | -26.4 | -37.2 | 100.0 |
| OL810B05 | 54.1 | 0.4 | 40.1 | 5.3 | 17.3 | 96.5 | -6.7 | -45.9 | 16.5 |
| OL810B04 | 55.5 | 0.4 | 44.9 | 0.0 | 49.9 | 133.3 | -0.5 | -52.6 | 47.9 |

Showing 1 to 10 of 10 entries

Dashboard
Site Info
Map View
Table View
Collector Details
Collector Settings
Site Health
Automation
Reports
Compliance/Alerts
User Settings Active Collectors: 10
Total CH4 Flow: 118 SCFM
Total LFG Flow: 216 SCFM
Total CO2: 36.4%
Total CH4: 56.6%

Sign Out

FIG. 17

AUTOMATED COMPLIANCE MEASUREMENT AND CONTROL FOR LANDFILL GAS EXTRACTION SYSTEMS

CROSS-REFERENCE TO RELATED APPLICATIONS

This application claims the benefit under 35 U.S.C. § 119(e) of U.S. provisional patent application Ser. No. 62/967,147, entitled "AUTOMATED COMPLIANCE MEASUREMENT AND CONTROL FOR LANDFILL GAS EXTRACTION SYSTEMS", filed Jan. 29, 2020, which is hereby incorporated by reference in its entirety herein.

FEDERALLY SPONSORED RESEARCH

This invention was made with government support under SBIR Phase II Award No. 1632439 awarded by the National Science Foundation. The government has certain rights in the invention.

FIELD

The present disclosure relates generally to monitoring and controlling extraction of gas from landfills.

BACKGROUND

Landfills typically produce landfill gas as a result of decomposition processes occurring in the waste, and methane is often a component of this landfill gas. In order to reduce emissions of methane and other contaminants in landfill gas, the landfill sites are typically capped with a layer of cover material and gas extraction systems are installed to pull landfill gas out before it can penetrate the cover layer and escape. At larger sites, these gas extraction systems can consist of a plurality of vertical and horizontal wells drilled into the landfill, which are connected with piping to one or more vacuum sources. The cover layer prevents gas from freely escaping, while the vacuum in the extraction wells pulls landfill gas into the collection system. A conventional landfill gas extraction well typically has a manual valve that adjusts the localized vacuum pressure in that well, as well as a set of ports for sampling the gas characteristics with a portable gas analyzer. Landfill gas is most often disposed of in a flare, processed for direct use, or used to power electricity generation equipment (such as generators or gas turbines).

The horizontal and vertical wells in the collection system typically consist of a length of perforated pipe connected to a length of solid pipe that rises through the surface of the landfill for wellhead access. The perforated pipe may be laid across the landfill during active dumping and subsequently buried (forming "horizontal wells") under additional lifts or inserted into a hole drilled through the landfill (traditional "vertical wells"). This pipe then acts as the gas extraction interface between the fill and the collection system. Additional extraction points may also exist with collection through leachate cleanouts, sumps, cisterns, temporary cover layers, and other points of fluid connection with the landfill mass.

SUMMARY

Some embodiments provide for a method for use by a system coupled to at least one sensor and at least one flow control mechanism of a gas extraction system, the system comprising at least one controller and being configured for use in connection with a landfill gas extraction process for extraction of landfill gas from a landfill via the gas extraction system. The method comprises: using the at least one controller of the system to perform: obtaining, based on at least one measurement made by the at least one sensor, at least one current value indicative of a selected characteristic of the landfill gas extraction process; determining, at discrete time intervals, whether the at least one current value satisfies at least one compliance criterion for the selected characteristic; and when it is determined that the at least one current value does not satisfy the at least one compliance criterion for the selected characteristic, performing a corrective action.

Some embodiments provide for a system coupled to at least one sensor and at least one flow control mechanism of a gas extraction system, the system being configured for use in connection with a landfill gas extraction process for extraction of landfill gas from a landfill via the gas extraction system, the gas extraction system. The system comprises: at least one controller configured to: obtain, based on at least one measurement made by the at least one sensor, at least one current value indicative of a selected characteristic of the landfill gas extraction process; determine, at discrete time intervals, whether the at least one current value satisfies at least one compliance criterion for the selected characteristic; and when it is determined that the at least one current value does not satisfy the at least one compliance criterion for the selected characteristic, perform a corrective action.

BRIEF DESCRIPTION OF THE DRAWINGS

Various non-limiting embodiments of the technology are described herein with reference to the following figures. It should be appreciated that the figures are not necessarily drawn to scale. Items appearing in multiple figures are indicated by the same reference numeral in all figures in which they appear. For purposes of clarity, not every component may be labeled in every drawing.

FIG. 11 illustrates an example record of calibration measurements obtained by a landfill gas extraction system, in accordance with some embodiments of the technology described herein.

FIGS. 12-17 are examples of a graphical user interface configured for use with a landfill gas extraction system, in accordance with some embodiments of the technology described herein.

DETAILED DESCRIPTION

Figure 1:
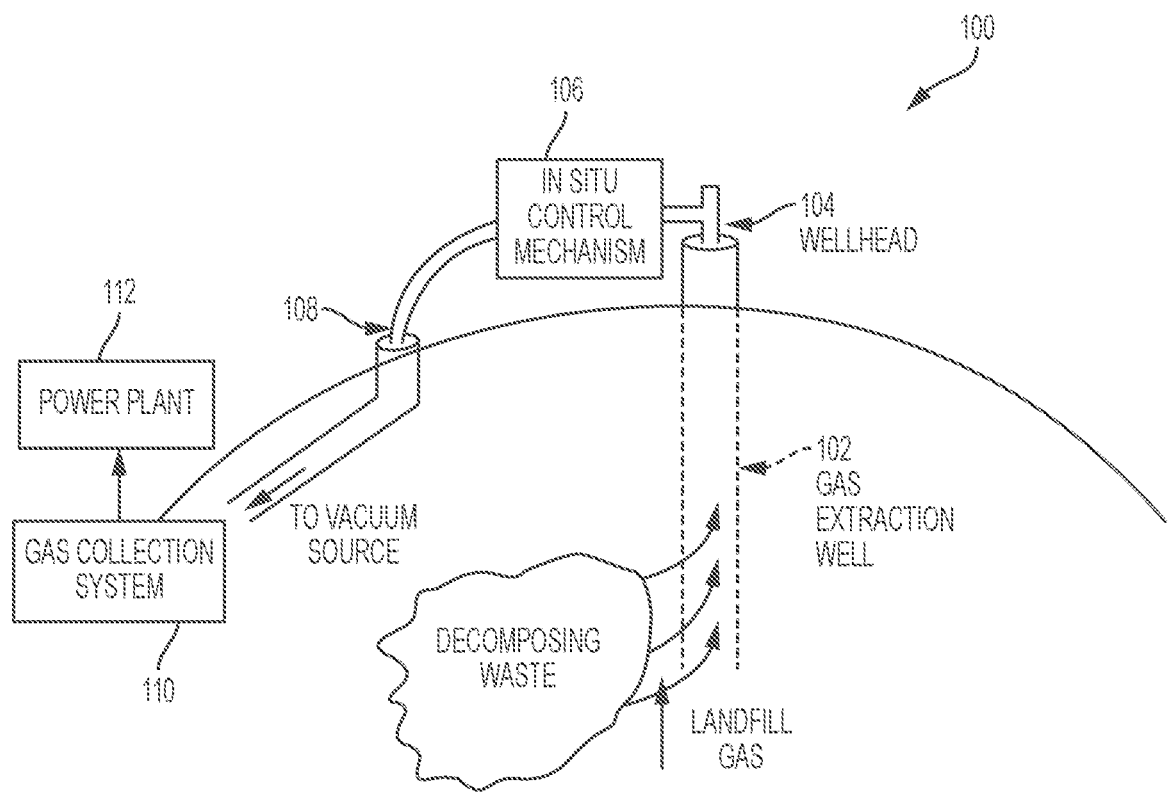
FIG. 1 is a schematic diagram of an example landfill gas extraction system, in accordance with some embodiments of the technology described herein.

Some conventional techniques for monitoring and controlling extraction of landfill gas from a landfill using a gas extraction system are imprecise and inefficient, and may be improved upon. When such techniques are used, the gas extracted from the landfill does not have desired properties, for example, because the composition of the extracted gas differs from a desired composition. Some techniques can also be counter-productive, for example, where the extraction process causes some or all of the bacteria that convert decomposition waste into methane to be destroyed, thereby reducing the energy content of the landfill gas, or where the extraction process results in emission of high levels of methane into the atmosphere. Such techniques can also lead to additional undesired and dangerous side effects, such as emission of odors from and underground fires in a landfill well.

Currently there are regulations applicable to landfills which govern the operation of landfill gas extraction systems. For example, certain regulations require operating values of selected characteristics of the landfill gas extraction process to remain below a threshold. When a value of a selected characteristic exceeds a threshold, the value is considered an "exceedance." Thus, monitoring and controlling landfill gas extraction based on these selected characteristics may prevent dangerous conditions resulting from exceedances of the selected characteristics from occurring as well as provide for compliance with applicable regulations. Other regulations further require documentation of extraction measurements and control actions to be kept, in addition to documentation of sensor calibration intervals, and calibration measurements.

The inventors have recognized that automatically monitoring and controlling extraction of landfill gas based on one or more compliance parameters improves upon conventional techniques by overcoming at least some of the deficiencies of conventional landfill gas extraction techniques while also providing for automated compliance with applicable regulations governing landfill gas extraction. For example, controlling extraction of landfill gas to ensure that a value of a selected characteristic of the landfill gas extraction process satisfies a compliance criterion, and performing a corrective action when the compliance criterion is not satisfied, can prevent dangerous conditions from developing within or around the landfill (e.g., by reducing the amount of harmful and/or foul-smelling gas emitted into the atmosphere, and/or preventing underground fires from occurring at the landfill site). In some embodiments, the monitored characteristics include one or more of oxygen concentration of extracted landfill gas, temperature of extracted landfill gas, and gauge pressure applied to a collection wellhead of the gas extraction system. In some embodiments, performing a corrective action includes adjusting a flow control mechanism of the gas extraction system to change a flow rate of the extracted landfill gas.

The inventors have developed techniques for monitoring and controlling landfill gas extraction with little to no need for manual oversight of the gas extraction system. For example, the inventors have recognized that automatic monitoring of certain characteristics of the landfill gas extraction process provides a significant reduction in time and cost for landfill gas extraction as compared to manual monitoring techniques. Automatic monitoring and control of the landfill gas extraction system when a measured characteristic does not satisfy certain compliance criteria also provides for potentially dangerous conditions at the landfill site to be remedied in an efficient manner. Further aspects of the technology described herein also relate to methods for automatically recording measurements obtained by the landfill gas extraction system, as well as other data related to the landfill gas extraction process, and in some embodiments, automatically generating a report based on these measurements. Implementing the monitoring, controlling, and recording methods described herein also provides for automated compliance with regulations governing landfill gas extraction.

In some embodiments, the methods described herein for controlling extraction of landfill gas may be implemented in conjunction with methods for optimizing methane content in extracted landfill gas. Aspects of the technology described herein may further be implemented as a method for automatically monitoring health of components of the gas extraction system by automatically detecting when a component of a landfill gas extraction system may need to be repaired and/or replaced.

Accordingly, some embodiments provide for a method for use by a system coupled to at least one sensor and at least one flow control mechanism (e.g., a valve) of a gas extraction system, the system comprising at least one controller and being configured for use in connection with a landfill gas extraction process for extraction of landfill gas from a landfill via the gas extraction system. The method comprises using the at least one controller to perform: obtaining (in some embodiments, according to a predefined schedule, for example, hourly, daily, weekly, and/or monthly), based on at least one measurement made by at least one sensor, at least one current value indicative of a selected characteristic of the landfill gas extraction process (e.g., one or more of oxygen concentration of extracted landfill gas, gas temperature of extracted landfill gas, and gauge pressure applied to a collection wellhead); determining, at discrete time intervals (e.g., according to a predefined schedule, for example, hourly, daily, weekly, and/or monthly), whether the at least one current value satisfies at least one compliance criterion for the selected characteristic (e.g., determining whether the current value is less than a threshold for the selected characteristic, for example, less than 5% for oxygen concentration, less than 55 degrees Celsius for gas temperature, negative gauge pressure for gauge pressure applied to the collection wellhead, and/or less than or equal to a threshold, greater than a threshold, greater than or equal to a threshold, and/or within a range of thresholds); and when it is determined that the at least one current value does not satisfy the at least one compliance criterion for the selected characteristic, performing a corrective action (e.g., adjusting the flow control mechanism to change a flow rate of landfill gas being extracted from the landfill, for example, by opening or closing a valve of the flow control mechanism to a greater degree, and, in some embodiments, generating an alert and/or notifying a user, opening or closing the valve in predefined increments, and/or generating an electronic alert such as a text message, phone call, email, push notification and/or alarm, for example, indicating an action to be performed by a user, such as repairing a leak in the gas extraction system, and/or replacing a component of the gas extraction system).

In some embodiments, performing the corrective action when the selected characteristic is oxygen concentration includes adjusting the at least one flow control mechanism to decrease flow rate of extracted landfill gas, and/or generating an electronic alert instructing a user to repair a leak in the gas extraction system. In some embodiments, performing the corrective action when the selected characteristic is gas temperature includes generating an alert. In some embodiments, performing the corrective action when the selected characteristic is gauge pressure includes adjusting the at least one flow control mechanism to increase flow rate of extracted landfill gas.

In some embodiments, the at least one current value is obtained for each of oxygen concentration, gauge pressure, and gas temperature, and the at least one current value for oxygen is obtained according to a first time interval (e.g., hourly and/or daily), the at least one current value for gauge pressure is obtained according to a second time interval (e.g., weekly and/or monthly), and the at least one current value for gas temperature is obtained according to a third time interval (e.g., weekly and/or monthly), and, in some embodiments, the method further comprises determining whether at least one value for each of oxygen concentration, gas temperature, and gauge pressure satisfy at least one compliance criterion for oxygen concentration, gas temperature, and gauge pressure, respectively and further, in some embodiments, may include using the at least one controller to calibrate the at least one sensor using at least one calibration gas comprising oxygen.

In some embodiments, the method further comprises obtaining, based on measurements made by the at least one sensor, at least one subsequent value indicative the selected characteristic (e.g., oxygen concentration of extracted landfill gas, gas temperature of extracted landfill gas, gauge pressure applied to a collection wellhead) and at least one additional characteristic of the landfill gas extraction process (e.g., one or more of oxygen concentration of extracted landfill gas, gas temperature of extracted landfill gas, and/or gauge pressure applied to a collection well head), after performing the corrective action, and, in some embodiments, after obtaining the at least one subsequent value indicative of the selected characteristic and the at least one value indicative of the at least one additional characteristic, the method may further include determining whether at least one subsequent value indicative of the selected characteristic (e.g., oxygen concentration, gas temperature, and/or gauge pressure) satisfies the at least one compliance criterion for the selected characteristic and whether the at least one value indicative of the at least one additional characteristic (e.g., one or more of oxygen concentration, gas temperature, and/or gauge pressure) satisfies at least one compliance criterion for the additional characteristic (e.g., the subsequent value being less than a threshold for the additional characteristic, for example, less than 5% for oxygen concentration, less than 55 degrees Celsius for gas temperature, and/or negative gauge pressure for gauge pressure applied to a collection wellhead) and/or determining whether the at least one subsequent value indicative of the selected characteristic (e.g., a subsequent value for oxygen concentration, gas temperature, and/or gauge pressure) is less than the at least one current value of the selected characteristic, and notifying a user (e.g., generating an alarm, transmitting a message, for example, by email, text message, push notification and/or through a graphical user interface) when the at least one subsequent value of the selected characteristic is not less than the at least one current value of the selected characteristic. In some embodiments, the at least one controller is configured to automatically perform the corrective action when it is determined that the at least one current value of the selected characteristic does not satisfy the at least one compliance criterion for the selected characteristic.

In some embodiments, the at least one additional characteristic comprises at least one first additional characteristic and at least one second additional characteristic, and the at least one first additional characteristic, the at least one second additional characteristic, and the selected characteristic are different from each other and, in some embodiments, are selected from the group consisting of oxygen concentration, gas temperature, and gauge pressure applied to the collection wellhead of the gas extraction system. In some embodiments, the method further comprises using the at least one controller to perform: after obtaining the at least one subsequent value for the selected characteristic and at least one value for the first additional characteristic and the second additional characteristic: determining whether at least one subsequent value indicative of the selected characteristic satisfies the at least one compliance criterion for the selected characteristic; determining whether the at least one value indicative of the first additional characteristic satisfies at least one compliance criterion for the first additional characteristic; and determining whether the at least one value indicative of the second additional characteristic satisfies at least one compliance criterion for the second additional characteristic.

In some embodiments, the method further comprises: when it is determined that the subsequent value indicative of the selected characteristic satisfies the at least one compliance criterion for the selected characteristic, the at least one value indicative of the first additional characteristic satisfies the at least one compliance criterion for the first additional characteristic, and the at least one value indicative of the second additional characteristic satisfies the at least one compliance criterion for the second additional characteristic: using the at least one controller to determine a time interval between a first time when the at least one controller determined the at least one current value indicative of the selected characteristic does not satisfy a compliance criterion and a second time when the at least one controller determined that the subsequent value indicative of the selected characteristic satisfies the at least one compliance criterion for the selected characteristic, the at least one value indicative of the first additional characteristic satisfies the at least one compliance criterion for the first additional characteristic, and the at least one value indicative of the second additional characteristic satisfies the at least one compliance criterion for the second additional characteristic; and using the at least one controller to record the time interval into a database, and, in some embodiments, the at least one controller to record, in the database, one or more values obtained by the at least one sensor indicative of the selected characteristic, the first additional characteristic, and/or the second additional characteristic during the first time interval and one or more corrective actions performed during the time interval. In some embodiments the method further comprises using the at least one controller to instruct the system to return to an initial mode of operation when it is determined that the subsequent value indicative of the selected characteristic satisfies the at least one compliance criterion for the selected characteristic, the at least one value indicative of the first additional characteristic satisfies the at least one compliance criterion for the first additional characteristic, and the at least one value indicative of the second additional characteristic satisfies the at least one compliance criterion for the second additional characteristic.

In some embodiments, the method further comprises obtaining a measure of concentration of methane in the landfill gas being extracted from the landfill (in some embodiments, according to a predefined schedule, e.g., at least once per day, at least once per hour, etc.); determining whether the measure of concentration of methane is either less than a first threshold concentration (e.g., 45% methane concentration, 55% methane concentration) or greater than a second threshold concentration (e.g., 55% methane concentration, 65% methane concentration); when it is determined that the measure of concentration of methane is less than the first threshold concentration, automatically controlling the at least one flow control mechanism to increase concentration of methane in landfill gas being extracted from the landfill (e.g., by decreasing flow rate of extracted landfill gas); and when it is determined that the measure of concentration of methane is greater than the second threshold concentration, automatically controlling the at least one flow control mechanism to decrease concentration of methane in landfill gas being extracted from the landfill (e.g., by increasing flow rate of extracted landfill gas), and, in some embodiments, further comprises automatically controlling the at least one flow control mechanism based at least in part on aggregate gas composition and flow data (e.g., power generation requirements, power generation capacity, current power generation) from a plant receiving the landfill gas being extracted from the landfill.

In some embodiments, the method further comprises obtaining, based on at least one measurement from the at least one sensor, a concentration of a constituent gas (e.g., methane, carbon dioxide, oxygen, and/or nitrogen) in a first sample of calibration gas, wherein the first sample of calibration gas comprises a first gas having a known composition; obtaining, based on at least one measurement from the at least one sensor, a concentration of the constituent gas in a second sample of calibration gas, wherein the second sample of calibration gas comprises a second gas having a known composition different than the known composition of the first gas (e.g., the second sample of calibration gas includes oxygen and the first sample of calibration gas does not include oxygen, and, in some embodiments, the second sample of calibration gas comprises no less than approximately 10% oxygen and no more than approximately 12% oxygen, the second sample of calibration gas comprises a sample of ambient air outside the gas extraction system, and/or the first sample of calibration gas comprises 35% $CO_2$, 50% $CH_4$, 15% $N_2$ and 0% $O_2$); and automatically calibrating the at least one sensor based on a comparison between the obtained concentrations of the constituent gas in the first and second samples of calibration gas and an expected concentration of the constituent gas in the first and second samples of calibration gas (in some embodiments, according to a predefined schedule and/or upon receiving a command from a user, for example, receiving a command from a user through a graphical user interface). In some embodiments, the method further comprises using the at least one controller to automatically calibrate the at least one sensor: prior to obtaining the at least one current value indicative of the selected characteristic, after performing the corrective action and prior to obtaining at least one subsequent value of the selected characteristic, and/or when it is determined that the at least one current value of the selected characteristic does not satisfy the at least one compliance criterion for the selected characteristic (e.g., when the selected characteristic is oxygen concentration and the at least one current value is not less than 5%, when the selected characteristic is gas temperature and the at least one current value is not less than 55 degrees Celsius, and/or when the selected characteristic is gauge pressure applied to the collection wellhead and the at least one current value is non-negative). In some embodiments, the method further comprises using the at least one controller to store the obtained concentrations of the constituent gas in the first and second samples of calibration gas in a database.

In some embodiments, the method further comprises recording the at least one current value in a database and labeling the at least one current value as an exceedance in the database when it is determined that the at least one current value does not satisfy the at least one compliance criterion (e.g., the current value exceeds a threshold value), and in some embodiments, may further include notifying a user (e.g., generating an electronic alert such as an alarm, email, text message, push notification, phone call, and/or a display through a graphical user interface) when the at least one current value does not satisfy the at least one compliance criterion. In some embodiments, the method further comprises automatically recording the at least one current value in a database when it is determined that the at least one current value does not satisfy the at least one compliance criterion for the selected characteristic, and, in some embodiments, further comprises, after performing the corrective action, obtaining, based on at least one measurement made by the at least one sensor, at least one subsequent value indicative of the selected characteristic of the gas extraction process; and automatically recording the at least one subsequent value in the database. In some embodiments, the method further comprises determining whether the at least one subsequent value indicative of the selected characteristic of the landfill gas extraction process satisfies the at least one compliance criterion for the selected characteristic; and when it is determined that the at least one subsequent value satisfies the at least one compliance criterion: determining a length of time between the obtaining of the at least one current value and the obtaining of the at least one subsequent value, and automatically recording the length of time in the database (i.e., determining the approximate length of time that an exceedance existed for the selected characteristic). In some embodiments, the method further comprises automatically recording a location of the at least one sensor and/or at least one well, where the at least one measurement obtained by the at least one sensor is of extracted landfill gas from the at least one well, in a database when it is determined that the at least one current value does not satisfy the at least one compliance criterion for the selected characteristic (i.e., determining the approximate location of the exceedance). In some embodiments, the method further comprises using the at least one controller to record a time at which the at least one measurement was made by the at least one sensor in a database when it is determined that the at least one current value of the selected characteristic does not satisfy the at least one compliance criterion for the selected characteristic.

In some embodiments, the method further comprises receiving user input via a graphical user interface, for example, user input indicating the at least one compliance criterion (e.g., indicating a threshold value that a parameter cannot exceed), and/or user input defining the corrective action (e.g., an increment to increase and/or decrease flow rate of extraction of landfill gas from the landfill). In some embodiments, the method further comprises using the at least one controller to display, via a graphical user interface, an indication that the at least one current value for the selected characteristic does not satisfy the at least one compliance criterion (e.g., displaying an indication that one or more characteristics of the landfill gas extraction process are at an exceedance).

Some embodiments of the technology further relate to a system for use in connection with a landfill gas extraction process for extraction of landfill gas from a landfill via a gas extraction system, the system being configured to perform the methods described herein.

The aspects and embodiments described above, as well as additional aspects and embodiments, are described further below. These aspects and/or embodiments may be used individually, all together, or in any combination, as the technology is not limited in this respect.

Figure 9:
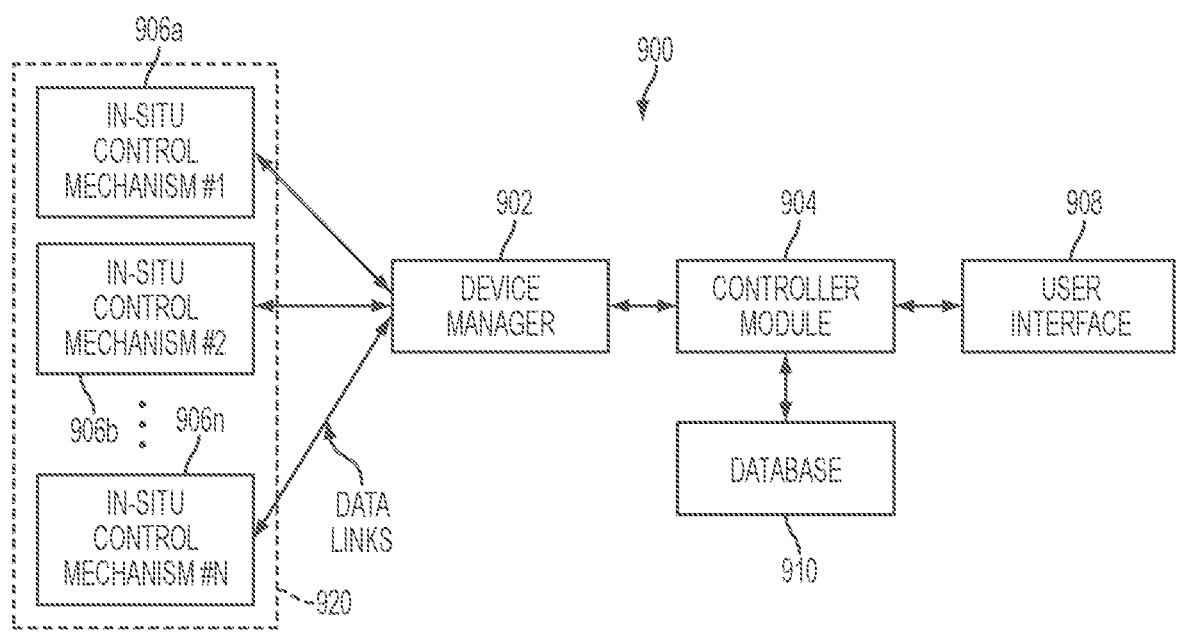
FIG. 9 is a block diagram of an example control system for controlling extraction of landfill gas from a landfill through a gas extraction system, in accordance with some embodiments of the technology described herein.

This disclosure describes devices and techniques for monitoring and controlling landfill gas extraction. FIG. 1 is a schematic diagram of an example landfill gas extraction system, in accordance with some embodiments of the technology described herein. In some embodiments, a landfill gas extraction system 100 may include one or more gas extraction wells 102 coupled to one or more wellheads 104. In some embodiments, each wellhead may be in fluid communication with a single, corresponding well. In some embodiments, the landfill gas extraction system 100 may include a gas extraction piping system 108 coupling the well(s) 102 to a gas collection system 110, and one or more In Situ Control Mechanisms 106 for controlling extraction of the landfill gas through the well(s) 102 and the gas extraction piping system 108 to the gas collection system 110. In some embodiments, gas collection system 110 may supply the extracted landfill gas to a gas-to-energy power plant 112, which may convert the landfill gas into electrical power (e.g., by burning the landfill gas to turn the rotor of a generator or turbine). In some embodiments, the In Situ Control Mechanism(s) 106 may operate (e.g., individually, in concert with each other, and/or under the control of a controller) to improve gas extraction efficiency and/or to control the extraction process for a variety of desired outcomes. In some embodiments the controller may be located remote from the In Situ Control Mechanisms (such a remotely located controller is not shown in FIG. 1, but is shown in FIG. 9 and described below.)

It should be appreciated that an In Situ Control Mechanism, as described herein, may control one or more parameters associated with a well, but is not a requirement that all In Situ Control Mechanism be physically located at that well. The In Situ Control Mechanism(s) may be disposed at any suitable location(s). In some embodiments, each In Situ Control Mechanism may be coupled to a single, corresponding well. In some embodiments, an In Situ Control Mechanism may be coupled to one or more wells. In some embodiments, some or all of the gas extraction wells in a landfill gas extraction system may be outfitted with an In Situ Control Mechanism 106, as depicted in FIG. 1. In some embodiments, an In Situ Control Mechanism 106 may be positioned at or adjacent to one or more junction points in the gas extraction piping system 108 (header junctions, or leachate junctions, or others) to control the performance of an entire section of piping. In some embodiments, an In Situ Control Mechanism 106 may be positioned between the gas extraction well 102 and the gas collection system 110 such that gas coming from the well flows through the In Situ Control Mechanism 106 on its way to the rest of the collection system. The In Situ Control Mechanism 106 may be installed permanently in a suitable location (e.g., in, on, adjacent to, and/or near a well and/or gas extraction piping), or may be moved from location to location (e.g., well to well) over time.

The gas extraction system 100 may include a Gas Analyzer which may be installed in-line with the landfill gas collection system. A system comprised of a plurality of these units is meant to alleviate the need for a constant presence of dedicated personnel attending to each wellhead, so it may be advantageous that the hardware perform reliably with minimal need for maintenance and technician attention. Such units may contain wetted sensors (sensors that require a fluid connection with the gas stream or a sample of the gas to perform the desired function—including pressure sensors and gas composition sensors that require immersion in the media). In some embodiments, one or more sensors are additionally or alternatively disposed elsewhere in the landfill gas extraction system as well as external to the landfill gas extraction system. In some embodiments, pre-treatment mechanisms are implemented in the gas extraction system, as described herein, to mitigate the particulate, humidity and corrosive properties of a landfill gas stream to extend the lifetime and accuracy of any wetted sensors.

Figure 2:
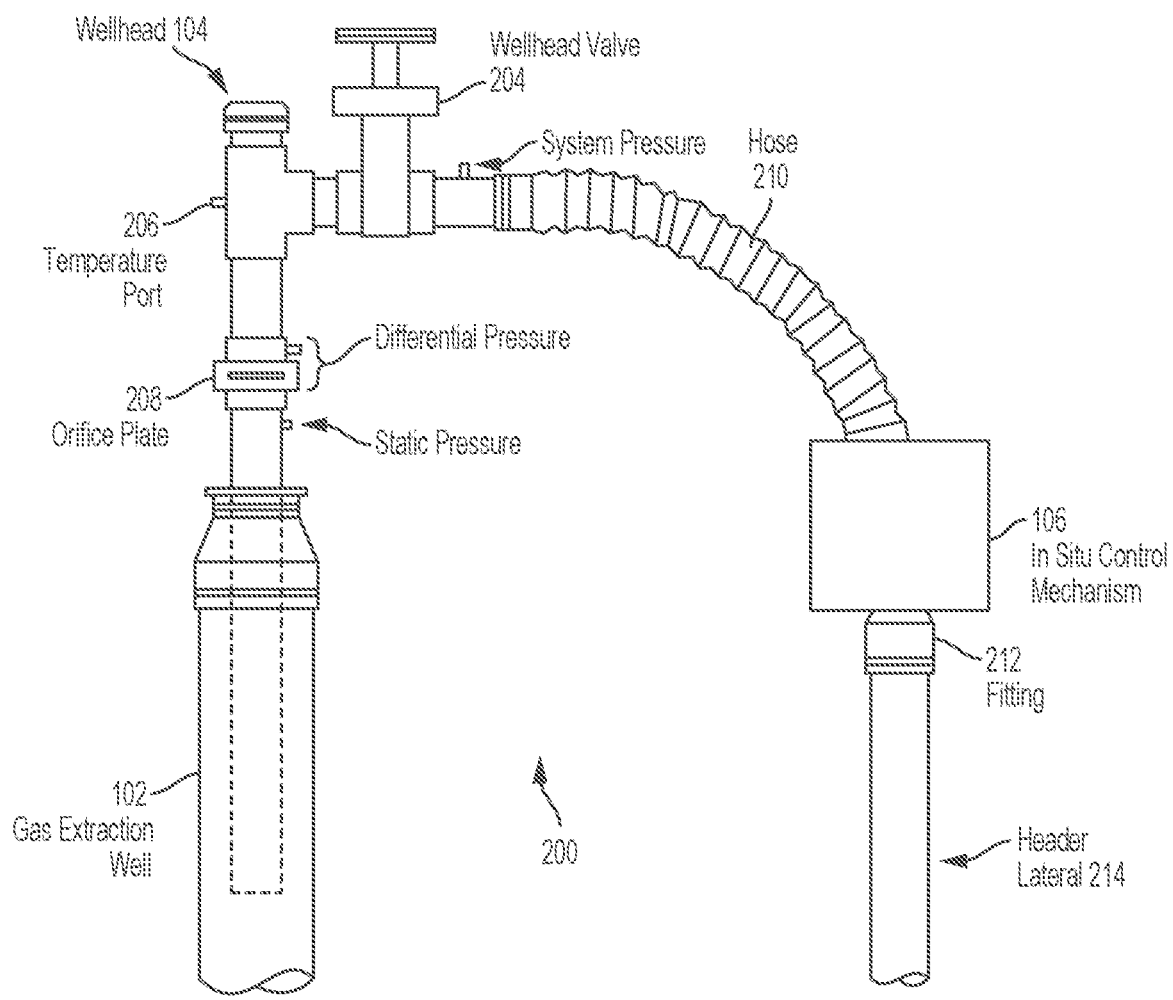
FIG. 2 is a schematic diagram illustrating additional aspects of the example landfill gas extraction system of FIG. 1, in accordance with some embodiments of the technology described herein.

FIG. 2 is a schematic diagram illustrating additional aspects of the example landfill gas extraction system of FIG. 1, in accordance with some embodiments of the technology described herein. For example, FIG. 2 illustrates various sensors that can be implemented in the landfill gas extraction system. The sensors may be configured to measure characteristics of the landfill gas extraction process, including, without limitation, attributes of the landfill, attributes of the landfill gas, attributes of an area adjacent to the landfill, and/or attributes of the landfill's gas extraction system. Measurements obtained by the sensors of the gas extraction system may be monitored and used to control landfill gas extraction from the landfill to ensure safe operation of the gas extraction system while also, in some embodiments, optimizing the quality of the landfill gas extracted from the landfill, as well as providing for automated compliance with regulations governing gas extraction.

As shown in FIG. 2, the gas extraction system 200 is coupled to a gas extraction well 102 for extracting landfill gas from a landfill. Flow rate of the extracted landfill gas may be measured by an orifice plate 208, for example, which the landfill gas passes through during extraction. Flow rate of the extracted landfill gas may be controlled by adjustments made to a flow control mechanism, which may include the wellhead valve 204 of the collection wellhead 104 shown in FIG. 1. The extracted landfill gas may be caused to flow through hose 210, for example, using a pump (not shown), and to a gas collection system, such as gas collection system 110 shown in FIG. 1. The gas extraction system 200 may include the In Situ Control Mechanism 106 which may be disposed along the path of the hose 210. As described herein, the In Situ Control Mechanism 106 may be configured to assist in controlling extraction of landfill gas. The extracted landfill gas may flow through the In Situ Control Mechanism 106 and to a header lateral 214 coupled to the In Situ Control Mechanism 106 by a fitting 212, which may facilitate flow of the extracted landfill gas to a gas collection system 110, as shown in FIG. 1.

Certain characteristics of the landfill gas extraction process can heavily impact the conditions of the extracted landfill gas and surrounding conditions at the landfill site. The inventors have recognized that monitoring certain characteristics of the landfill gas extraction process and controlling extraction based on values of these characteristics can ensure safe landfill gas extraction with optimal gas quality. For example, insufficient vacuum pressure in a given extraction well can lead to buildup of gas underground, and may result in fugitive emissions as excess gas permeates the cover of the landfill and escapes into the atmosphere. On the other hand, excessive vacuum pressure can pull atmospheric oxygen into the waste mass, upsetting the anaerobic conditions that are necessary for methane generation, and if left uncorrected, may lead to elevated subterranean temperatures and a variety of associated problems (including, but not limited to, subsurface fires, ground instability, damage to collection infrastructure, runaway exothermic reactions, odors, and the release of toxins and other chemicals that might otherwise remain trapped underground). As environmental and other conditions in the landfill change, the rates of gas generation and extraction can become unbalanced, requiring an adjustment of the extraction pressure in order to avoid the problems above. Likewise, excess amounts of $O_2$ and high temperatures may lead to similar problems. Thus, the inventors have recognized that it is advantageous to monitor values of oxygen concentration in extracted landfill gas, gas temperature, and gauge pressure applied to a collection wellhead of the gas extraction system, and control extraction based on these values in order to prevent or mitigate the above-described problems.

In some embodiments, the gas extraction system 200 includes one or more pressure sensors to measure pressure in and/or around the gas extraction system. For example, the gas extraction system may include external pressure sensors configured to measure atmospheric air pressure. Other pressure sensors may be implemented on or internal to the gas extraction system, for example, in a Gas Analyzer of the In Situ Control Mechanism 106, described herein.

In some embodiments, for example, as illustrated in FIG. 2, the landfill gas extraction system measures static pressure (also referred to herein as gauge pressure applied to the collection wellhead, or simply gauge pressure) at a location below the orifice plate on a landfill gas collection wellhead. Static pressure is measured using a pressure sensor coupled to the gas extraction system 200 at a location below the orifice plate 208, when considering the direction of the flow of extracted landfill gas. An additional pressure port for measuring system pressure may be disposed above the orifice plate 208 and after the wellhead valve 204, as shown in FIG. 2. Measurements for the static pressure below the orifice plate 208 and system pressure above the orifice plate 208 may be used to calculate a differential pressure across the orifice plate 208.

The gas extraction system 200 may measure landfill gas temperature using a temperature sensor, such as a thermistor, coupled to the temperature port 206, at a location above the orifice plate 208 on the landfill gas collection wellhead 104 when considering the direction of landfill gas flow. Although the illustrated embodiment shows the temperature port 206 being disposed above the orifice plate 208, in other embodiments, one or more temperature sensors may additionally or alternatively be coupled to the gas extraction system 200 at other locations, for example, coupled to a Gas Analyzer of the In Situ Control Mechanism 106 as described herein. Although not shown in the illustrated embodiment, additional temperature sensors may be implemented for measuring atmospheric temperature.

One or more sensors for measuring oxygen concentration may be implemented in the gas extraction system, for example, coupled to a Gas Analyzer of the In Situ Control Mechanism 106 as described herein. In some embodiments, the gas extraction system 200 may implement an oxygen sensor which uses a quenched fluorescence-based measurement method, for example, a LuminOx $O_2$ sensor.

As described herein, the gas extraction system 200 may be coupled to various sensors for obtaining measurements for monitoring and controlling the extraction of landfill gas through the gas extraction system. In some embodiments, the sensors are coupled to the gas extraction system, while not being a part of the gas extraction system. In other embodiments, one or more of the sensors are part of the gas extraction system itself.

Figure 3A:
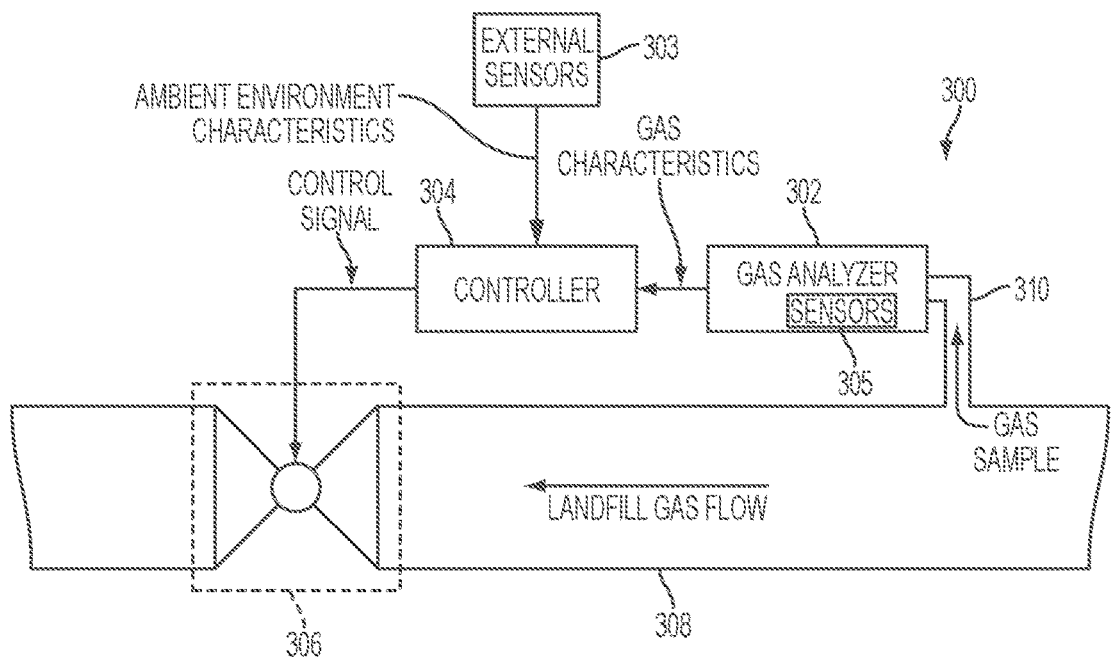
FIG. 3A is a block diagram of a control mechanism of the example gas extraction system of FIG. 1, in accordance with some embodiments of the technology described herein.

As described herein, a gas extraction system may include an In Situ Control Mechanism for controlling the extraction of landfill gas from a landfill through the gas extraction system. FIG. 3A is a block diagram of a control mechanism of the example gas extraction system of FIG. 1, in accordance with some embodiments of the technology described herein.

In some embodiments, an In Situ Control Mechanism 300 may include one or more mechanisms configured to control the flow rate of landfill gas from one or more wells to gas collection system 110 through gas extraction piping system 108. Any suitable flow control mechanism 306 may be used, including, without limitation, a valve, such as the wellhead valve 204, and/or any other suitable type of flow control mechanism.

In some embodiments, an In Situ Control Mechanism 300 may include one or more actuation devices configured to control operation of the one or more flow control mechanisms (e.g., to open a flow control mechanism, close a flow control mechanism, and/or adjust a setting of a flow control mechanism) and/or one or more sensor devices configured to sense one or more attributes associated with the landfill, as described. In some embodiments, an In Situ Control Mechanism 300 may include a controller 304 configured to determine the settings to be applied to the one or more flow control mechanisms and/or the one or more sensors (e.g., via the actuation devices), and/or configured to apply the settings to the one or more flow control mechanisms and/or the one or more sensors (e.g., via the actuation devices). In some embodiments, the settings may be determined remotely and communicated to the In Situ Control Mechanism 300 (e.g., by a remotely located controller) using any suitable communication technique, including, without limitation, wireless communication, wired communication, and/or power line communication.

In some embodiments, the one or more sensor devices may include a Gas Analyzer 302. In some embodiments, a Gas Analyzer 302 may collect a sample of landfill gas from the gas extraction piping 308 through an input port 310, determine (e.g., compute, measure and/or sense) one or more characteristics of that gas, and/or report the one or more characteristics of the gas to a controller (e.g., local controller 304 and/or a remotely located controller). In some embodiments, the Gas Analyzer 302 may determine the gas temperature, pressure, flow rate, humidity, density, gas composition (partial pressure or concentration of methane, oxygen, carbon dioxide, carbon monoxide, hydrogen sulfide, nitrogen and/or any other suitable gas) and/or any other characteristics of the landfill gas coming from the gas extraction well(s) upstream from the location where the In Situ Control Mechanism 300 is installed. The gas characteristics may be sampled once in each reading, or may be sampled many times and statistics about the distribution of values may be determined. The gas characteristics may be continuously determined, or they may be determined at discrete time intervals. In some embodiments, the Gas Analyzer 300 may analyze gas in the main flow of landfill gas (e.g., within gas extraction piping 308). In some embodiments, the Gas Analyzer 302 may draw a small sample of gas into a separate chamber for analysis. In some embodiments, certain parameters (for example flow rate, pressure, temperature, humidity, and the like) may be measured in the main gas stream (e.g., may be measured by sensors disposed directly within extraction gas piping), and others may be analyzed in a separate chamber.

In some embodiments, one or more external sensors 303 are provided for obtaining measurements of ambient environment characteristics (e.g., ambient pressure, ambient temperature, humidity, a characteristic of ambient precipitation, etc.). The controller 304 may be configured to receive data from the one or more external sensors 303 and control according to the external sensor measurements, for example, according to the methods described herein.

In order to improve measurement accuracy, measurement resolution, measurement repeatability, sensor lifetime, and/or sensor reliability, a sample of gas from the well may be pre-treated before analysis, which pre-treatment may include heating, cooling, drying, and/or any other suitable pre-treatment processing (e.g., through forced condensation, passing through a desiccant, or any other suitable technique), filtered to remove particles, filtered to remove contaminants or other chemicals, pressurized, de-pressurized, and/or otherwise treated before being analyzed. After analyzing and reporting gas characteristics (e.g., to local controller 304 and/or to a remotely located controller), the Gas Analyzer may purge the gas sample from the chamber and vent it to the atmosphere, or return it to the main gas flow. In some embodiments, the analyzed gas sample may be purged prior to reporting the gas characteristics to a controller.

Figure 3B:
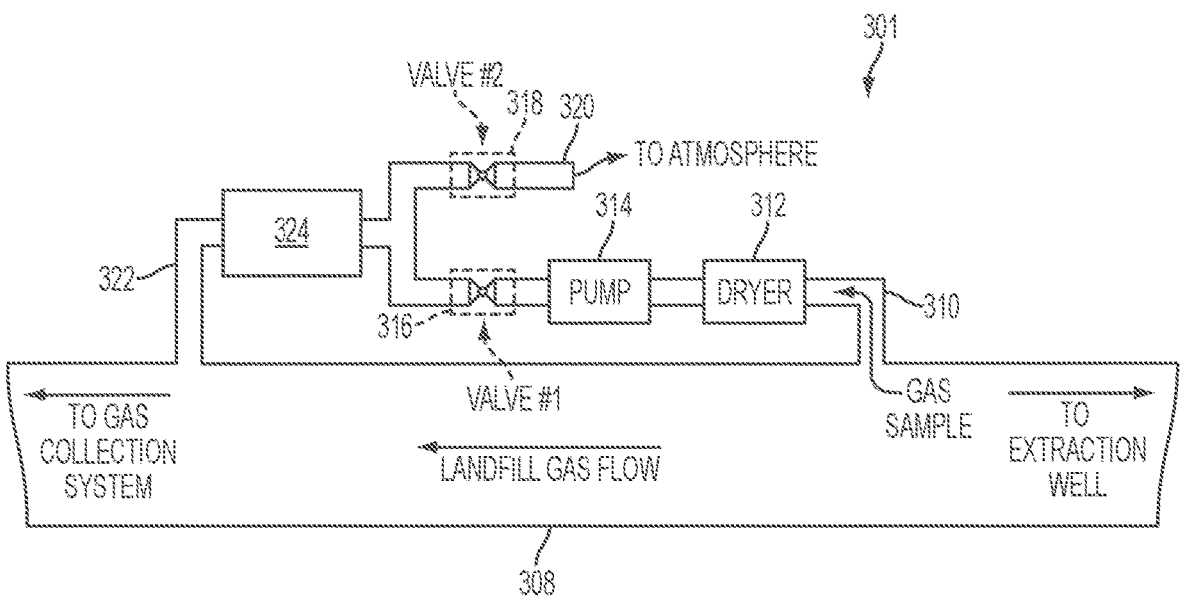
FIG. 3B is a block diagram of a Gas Analyzer of the control mechanism of FIG. 3A, in accordance with some embodiments of the technology described herein.

FIG. 3B is a block diagram of a Gas Analyzer of the control mechanism of FIG. 3A, in accordance with some embodiments of the technology described herein. In the Gas Analyzer 301 of FIG. 3B and other arrangements not explicitly described here, a small sample of landfill gas may be taken into the Gas Analyzer 301 through input port 310 (e.g., from the main flow of landfill gas in gas extraction piping 308 between the gas extraction well and the gas collection system) and sent through a drying element 312 and a series of one or more flow control mechanisms (e.g., valves) before entering the sample chamber 324. In some embodiments, at the beginning and end of a gas measurement cycle, both valves 316 and 318 are in the closed state. Valve 316 may be opened and the pump 314 may be turned on in order to draw a sample of landfill gas through the drying element 312 and into the sample chamber 324 for analysis. At the end of a measurement cycle, the pump 314 may be turned off and valve 316 may be closed to stop the flow of gas into the sample chamber 324. In some embodiments, the gas sample may be purged from sample chamber 324 by opening valve 318. Under typical operating conditions, the gas collection system and gas extraction well(s) may be at negative pressure (i.e., operating under vacuum conditions) relative to atmospheric pressure, such that opening valve 318 may pull ambient air through the Gas Analyzer 301 to purge the sample chamber 324 of landfill gas. In some embodiments, one or more valves of Gas Analyzer 301 may be toggled and a pump (e.g., pump 314) may be activated to force purge sample chamber 324 with ambient air. (Although not shown, one of ordinary skill in the art would understand that a valve may be placed between pump 314 and input port 310, and that sample chamber 324 may be force purged by closing this valve and by opening valves between pump 314 and atmospheric port 320.) After purging the gas sample from Gas Analyzer 300, valve 318 may be closed to stop atmospheric air from leaking into the gas collection system.

Configurations that perform a similar function to the embodiment of FIGS. 3A and 3B, and which, while not described explicitly here, are within the scope of the present disclosure. For example, an additional valve may be added after the Gas Analyzer (e.g., in a port 322 coupling the sample chamber 324 to the gas extraction piping 308), for additional control or to prevent backflow into the sample chamber. Additionally, the Gas Analyzer 301 may be outfitted with additional modules to provide other pre-treatment of the gas in addition to or in alternative to drying (for example, particle filtering, removal or deactivation of hydrogen sulfide or other chemicals, etc.).

In some embodiments, the Gas Analyzer may utilize non-dispersive infrared (NDIR) sensors, catalytic beads, electrochemical sensors, pellistors, photoionization detectors, zirconium oxide sensors, thermal conductivity detectors, and/or any other sensing technology. Flow rate may be measured by a pressure differential across a venturi, orifice plate, or other restriction to the flow of gas; by pitot tube, mechanical flow meter, heated wire or thermal mass flow meter, and/or using any other suitable technique. Temperature may be measured with a thermocouple, a negative or positive temperature coefficient resistor, capacitor, inductor, a semiconducting device, and/or using any other suitable technique. Temperature may be measured inside the well, in the main gas flow from the well to the collection system, inside a sampling chamber, outside of the control mechanism (e.g., ambient atmospheric temperature), and/or at any other suitable point. Temperature, pressure, gas composition, and/or other readings from different points within the gas extraction well, the In Situ Control Mechanism, and/or the gas collection system may be used in conjunction with each other to obtain a more complete analysis of the operating state of the landfill gas collection system, as described herein.

Figure 4:
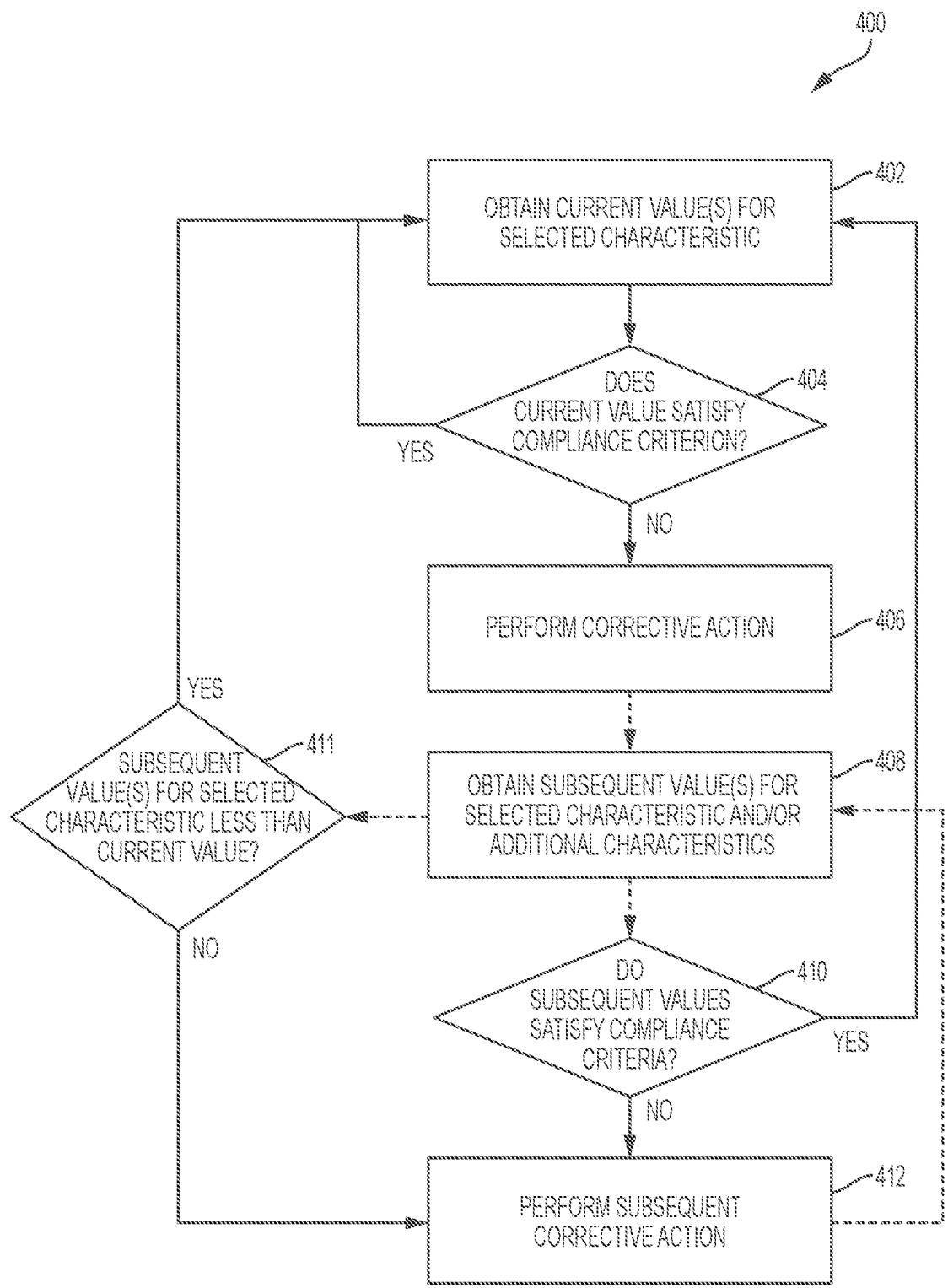
FIG. 4 is a flowchart of an example method for controlling extraction of landfill gas from a landfill through a gas extraction system, in accordance with some embodiments of the technology described herein.

As described herein, aspects of the technology relate to methods for ensuring measured values of one or more characteristics of the landfill gas extraction process satisfy a compliance criterion. FIG. 4 is a flowchart of an example method for controlling extraction of landfill gas from a landfill, in accordance with some embodiments of the technology described herein. The following methods can be implemented by any of the systems described herein, for example by one or more controllers of the gas extraction system 100.

Process 400 begins at act 402 where one or more current values for a selected characteristic are obtained, for example, by the gas extraction system. In some embodiments, for example, where the gas extraction system includes one or more sensors, obtaining the current value(s) may include instructing the sensor to obtain at least one measurement of the selected characteristic. In other embodiments, such as where the relevant sensor for the selected characteristic is external to the gas extraction system, obtaining the current value(s) may comprise receiving the current value(s) from an external device. In some embodiments, obtaining the current value(s) for the selected characteristic may be obtained indirectly. For example, where a gas contains a mixture of known components, the composition of a constituent gas may be calculated by obtaining values for all but one of constituent gasses in the mixture, and calculating the balance composition of the mixture to determine the amount of the final constituent gas.

The selected characteristic may include one or more of a variety of parameters relevant to the landfill gas extraction process. For example, in some embodiments, the selected characteristic is oxygen concentration of extracted landfill gas, and obtaining the current value(s) for the selected characteristic includes obtaining one or more current values for oxygen concentration of the extracted landfill gas. In other embodiments, the selected characteristic is gas temperature of the extracted landfill gas. In other embodiments, the selected characteristic is gauge pressure applied to the collection wellhead. The inventors have recognized that choosing the selected characteristic from one or more of oxygen concentration, gas temperature, and gauge pressure is advantageous as it provides for safer operation of the gas extraction process while optimizing the quality of the extracted gas and enabling automatic compliance with applicable regulations. In other embodiments, however, the selected characteristic may additionally or alternatively include one or more of methane concentration of extracted landfill gas, carbon dioxide concentration of extracted landfill gas, nitrogen concentration of extracted landfill gas, and/or other suitable characteristics related to the landfill gas extraction process.

At step 404, the process 400 moves to a decision block where it is determined whether the at least one current value satisfies a compliance criterion. In some embodiments, the gas extraction system is configured to perform step 404, for example, using at least one controller of the gas extraction system. In other embodiments, an external device can be configured to perform step 404 and the gas extraction system can be configured to receive the determination at step 404 from the external device.

Determining whether the current value satisfies a compliance criterion may comprise comparing the current value to a target value to determine whether the current value is different from the target value. In some embodiments, determining whether the current value satisfies a compliance criterion includes determining whether the current value is less than, less than or equal to, greater than, and/or greater than or equal to a one or more selected thresholds. In some embodiments, determining whether the current value satisfies a compliance criterion comprises determining whether the current value is within a selected range.

The compliance criterion may be defined based on the selected characteristic. For example, the inventors have appreciated that certain working parameters for selected characteristics provide for safer landfill gas extraction processes which also optimize gas quality and provide for compliance with regulations governing landfill gas extraction. Examples of compliance criterions for various selected characteristics are described further herein.

In some embodiments, acts 402 and 404 can be performed at discrete time intervals. For example, obtaining the one or more current values for the selected characteristic and/or determining whether the current value(s) satisfies the compliance criterion can be performed repeatedly at predefined time intervals, such as hourly, daily, weekly, monthly, or any other time interval appropriate for the selected characteristic and the landfill gas extraction process. The time interval may depend on the selected characteristic. For example, some characteristics may require monitoring more frequently than other characteristics. In some embodiments, only one of acts 402 and 404 are performed at discrete time intervals while the other act is performed continuously or only upon initiation by a user.

At act 404, when it is determined that the current value(s) satisfies the compliance criterion, the process 400 may proceed through the yes branch to act 402, where another current value for the selected characteristic is obtained to allow for continuous monitoring of the landfill gas extraction process for compliance with the compliance criterion. Although not illustrated in FIG. 4, in some embodiments, if it is determined that the current value(s) satisfies the compliance criterion, the process 400 may end.

When it is determined, at act 404, that the current value(s) does not satisfy the compliance criterion, the process 400 moves through the no branch to act 406, where a corrective action is performed. When the current value is determined, at act 404, not to satisfy the compliance criterion, the gas extraction system may be operating at suboptimal or even dangerous conditions. The inventors have recognized that it is advantageous for the gas extraction system to automatically perform the corrective action at act 406 such that the gas extraction system can return to safe and optimal operating conditions as quickly as possible.

Although not shown in the illustrated embodiment, in some embodiments, process 400 may require multiple determinations at act 404 that the current value(s) does not satisfy the compliance criterion before performing a corrective action. In some embodiments, this may include making a determination using the same current value at least twice before performing the corrective action. In other embodiments, the determination at act 404 includes making multiple determinations as to whether multiple values for the selected characteristic satisfy the compliance criterion, respectively, before performing a corrective action.

Performing the corrective action can comprise a variety of different actions automatically performed by the gas extraction system. For example, the corrective action may comprise changing a flow rate of extracted landfill gas through the gas extraction system by adjusting a flow control mechanism of the gas extraction system. Adjusting the flow control mechanism may comprise opening or closing a valve of the flow control mechanism to a greater degree. In some embodiments, opening or closing a valve of the flow control mechanism comprises opening or closing a valve of the flow control mechanism in predefined increments. In some embodiments, performing the corrective action includes repairing a component of the gas extraction system or otherwise at the landfill, for example repairing a leak in well piping of the gas extraction system and/or generating an electronic alert instructing a user to do the same. In some embodiments, performing the corrective action may comprise replacing a component of the gas extraction system or otherwise at the landfill, for example, replacing a sensor of the gas extraction system, replacing a vacuum of the gas extraction system, or another component of the gas extraction system in need of replacement or repair, and/or generating an alert instructing a user to do the same. In some embodiments, performing the corrective action may include automatically notifying a governing body of the current value and requesting permission to continue extraction operations. In some embodiments, performing the corrective action may comprise notifying a user of the conditions of the gas extraction system, for example by an electronic alert such as a push notification, email, text message, phone call and/or by an alarm, and in some embodiments, may additionally or alternatively include instructing the user to take a subsequent corrective action, for example, any of the corrective actions described herein or other suitable corrective action.

The corrective action performed by the gas extraction system at step 406 may depend on the selected characteristic. Various examples of the method 400 are now provided herein with respect to certain selected characteristics.

In one embodiment of the example process 400, the selected characteristic is oxygen concentration of extracted landfill gas. At step 402, one or more current values for oxygen concentration is obtained by the gas extraction system, for example, by an oxygen sensor, such as sensors 305 shown in FIG. 3. In some embodiments, the gas extraction system includes the oxygen sensor, and in other embodiments, the gas extraction system is configured to receive the current value from an oxygen sensor external to the gas extraction system.

As described herein, act 402 may be performed on a frequent or predefined basis. For example, the current value for oxygen concentration may be obtained hourly, daily, weekly, monthly, or at any other suitable frequency. The inventors have recognized, however, that it is advantageous to obtain measurements of oxygen concentration relatively frequently, as the level of oxygen concentration in extracted landfill gas has a significant impact on both the safety of the gas extraction process and the quality of the landfill gas extracted from the landfill. Therefore, it is preferable to obtain the current value for oxygen concentration at least once an hour.

Measurements of oxygen concentration of the extracted landfill gas may be obtained simultaneously and/or concurrently, approximately at the same time, or at the same frequency as other measurements obtained by the gas extraction system. For example, measurements of oxygen concentration of the extracted landfill gas may be obtained at the same frequency as measurements of methane concentration of the extracted landfill gas, as part of a control process for optimizing methane content of the extracted landfill gas further described herein.

At step 404, it is determined whether the current value for oxygen concentration satisfies a compliance criterion for oxygen concentration. As described herein, the inventors have recognized that ensuring oxygen concentration of the extracted landfill gas does not exceed a threshold value is beneficial to optimize the methane content in the landfill gas, and to prevent dangerous conditions from occurring at the landfill site, such as subsurface fires, for example. Therefore, determining whether the current value for oxygen concentration satisfies the compliance criterion for oxygen concentration may include, at least, determining whether the current value of oxygen concentration is less than an upper threshold value.

In a preferred embodiment, the upper threshold value is 5% oxygen concentration. Therefore, step 404 includes determining whether the current value for oxygen concentration is less than or less than or equal to 5% oxygen concentration. However, in other embodiments, the compliance criterion may include determining whether the current value for oxygen concentration is less or less than or equal to than another threshold value, such as 4% oxygen concentration or 3% oxygen concentration, or any other suitable threshold value. In some embodiments, determining whether the current value for oxygen concentration satisfies the compliance criterion includes determining whether the current value for oxygen concentration is different than a target value. In some embodiments, determining whether the current value for oxygen concentration satisfies a compliance criterion includes determining whether the current value for oxygen concentration is within a range of concentrations. For example, a lower threshold may be approximately 2% oxygen concentration, and an upper threshold may be approximately 5%. Other suitable thresholds and ranges may be used at act 404 to determine whether the current value for oxygen concentration satisfies a compliance criterion, and aspects of the technology are not limited in this respect.

As described herein, act 404 may be performed on a frequent or predefined basis. For example, the determination as to whether an current value for oxygen concentration satisfies the compliance criterion may be made hourly, daily, weekly, monthly, or at any other suitable frequency. The inventors have recognized, however, that it is advantageous to determine whether an current value for oxygen concentration satisfies the compliance criterion relatively frequently, as the level of oxygen concentration in extracted landfill gas has a significant impact on both the safety of the gas extraction process and the quality of the landfill gas extracted from the landfill. Therefore, it is preferable to determine whether the current value for oxygen concentration satisfies the compliance criterion at least once an hour.

If, at step 404, that the current value for oxygen concentration does satisfy the compliance criterion, for example if the current value for oxygen concentration of the extracted landfill gas does not exceed 5% oxygen concentration, the process 400 can proceed through the yes branch back to step 402, where another current value for oxygen concentration is obtained. In this way, oxygen concentration of the extracted landfill gas can be continuously monitored. In other embodiments, although not shown in FIG. 4, the process can proceed to an end when the current value for oxygen concentration of the extracted landfill gas satisfies the compliance criterion.

If, at step 404, it is determined that the current value for oxygen concentration does not satisfy the compliance criterion, for example, if the current value for oxygen concentration of the extracted landfill gas exceeds 5% oxygen concentration, a corrective action can be performed automatically. As described herein, there are a variety of corrective actions that can be performed by the system. For oxygen concentration, the corrective action may comprise decreasing flow rate of the extracted landfill gas, for example by causing a valve of a flow control mechanism to close to a greater degree. The inventors have recognized that decreasing flow rate of extracted landfill gas can cause the oxygen concentration of the extracted landfill gas to decrease, as less oxygen is being pulled into the well piping from the atmosphere at lower flow rates. The inventors have further recognized that excess levels of oxygen concentration in extracted landfill gas may be caused by a leak in the gas extraction system. Therefore, in some embodiments, the corrective action may alternatively or additionally include instructing a user to perform a physical check of a component, repairing a leak in the gas extraction system and/or generating an electronic alert instructing a user to do the same, for example in well piping of the gas extraction system, replacing a component of the gas extraction system and/or generating an electronic alert instructing a user to do the same.

The inventors have recognized that nitrogen concentration in extracted landfill gas may behave similarly to oxygen concentration and can likewise be monitored with slight variations in the process 400. For example, high levels of nitrogen concentration in extracted landfill gas may increase danger of subsurface fires, or significantly inhibit anaerobic decomposition of landfill was by killing methanogens. Thus, it may be advantageous to apply process 400 to a landfill gas extraction system where nitrogen concentration is the selected characteristic.

Following process 400 where nitrogen concentration is the selected characteristic, at act 402, an current value of nitrogen concentration can be obtained. As described herein, nitrogen concentration may be obtained directly, for example, by a nitrogen sensor, or indirectly by calculating concentrations of other constituent gasses in extracted landfill gas and calculating the concentration of nitrogen as the balance. At step 404, the current value for nitrogen concentration of the extracted landfill gas is compared with one or more thresholds to determine whether the current value for nitrogen concentration satisfies a compliance criterion for nitrogen concentration. The compliance criterion may be that the nitrogen concentration of the extracted landfill gas does not exceed 20% nitrogen concentration, and thus act 404 can include determining whether the current value for nitrogen concentration of the extracted landfill gas exceeds 20% nitrogen concentration. As described herein, acts 402 and 404 may be performed at predefined intervals, and for nitrogen concentration, may preferably be performed hourly.

If, at act 404, it is determined that the current value for nitrogen concentration does satisfy the compliance criterion for nitrogen concentration, the process 400 can proceed to repeat act 402 and obtain an additional current value for nitrogen concentration, or alternatively, may end. If, at act 404 it is determined that the current value for nitrogen concentration of the extracted landfill gas does not satisfy the compliance criterion for nitrogen concentration, for example if the current value for nitrogen concentration of the extracted landfill gas exceeds 20%, the process 400 can proceed to act 406 where a corrective action is automatically performed. For nitrogen concentration, the corrective preferably action includes decreasing flow rate of the extracted landfill gas by adjusting a flow control mechanism of the gas extraction system.

Another example of a selected characteristic is gas temperature of extracted landfill gas. The inventors have recognized that elevated temperatures of extracted landfill gas may cause damage to collection infrastructure of the gas extraction system, among other issues, and thus it is advantageous to monitor gas temperature of the extracted landfill gas and automatically correct excessive temperatures, such as by using process 400 where gas temperature is the selected characteristic.

Following process 400 where gas temperature is the selected characteristic, at act 402, one or more current values of gas temperature may be obtained. For example, the current value(s) for gas temperatures may be obtained by a thermistor connected to the temperature port 206 shown in FIG. 2.

At act 404, a determination is made as to whether the current value for gas temperature satisfies a compliance criterion. As elevated gas temperatures can create dangerous conditions in the gas extraction system and at the landfill site, in some embodiments, the compliance criterion for gas temperature is the current value for gas temperature not exceeding an upper threshold. For example, the upper threshold may be 55 degrees Celsius (or 131 degrees Fahrenheit), and the compliance criterion is satisfied when the current value for gas temperature is less than 55 degrees Celsius, or does not exceed 55 degrees Celsius. In other embodiments, the upper threshold may be other temperatures, such as 50 degrees Celsius, or 45 degrees Celsius. In other embodiments, the compliance criterion may require gas temperature to be above a lower threshold, or within a range of temperatures between an upper and lower threshold. As described herein, acts 402 and 404 may be performed at predefined intervals, and for gas temperature, may preferably be performed once a month.

When it is determined, at act 404, that the current value for gas temperature satisfies the compliance criterion, the process 400 may return to act 402 to obtain an additional current value for gas temperature of extracted landfill gas, such that gas temperature of extracted landfill gas is being continuously monitored, or the process 400 may end. When it is determined, at act 404, that the current value for gas temperature does not satisfy the compliance criterion for gas temperature, for example, when the current value for gas temperature exceeds 55 degrees Celsius, the process 400 proceeds to act 406 where a corrective action is performed. For gas temperature, the corrective action preferably includes decreasing flow rate of the extracted landfill gas by adjusting a flow control mechanism of the gas extraction system. In other embodiments, the corrective action includes increasing flow rate of the extracted landfill gas by adjusting a flow control mechanism of the gas extraction system. The inventors have recognized that in some cases, it may be advantageous to increase flow rate when gas temperature exceeds the compliance criterion threshold in order to eliminate the excess heat in the landfill gas stream, while in other cases, it may be advantageous to decrease flow rate when gas temperature exceeds the compliance criterion threshold to reduce the amount of oxygen from the atmosphere being pulled into the landfill gas stream.

Another example of a selected characteristic is gauge pressure applied to the collection wellhead of the gas extraction system, also referred to herein as gauge pressure or static pressure. The inventors have recognized that elevated pressure within the gas extraction system, for example pressure within the gas extraction system that is higher than atmospheric pressure, may cause excess oxygen to be pulled from the atmosphere and into well piping of the gas extraction system, inhibiting methane generation and creating dangerous subsurface conditions. Thus, it is advantageous to monitor gauge pressure applied to the collection wellhead and automatically correct for elevated levels of gauge pressure, such as by using process 400 where gauge pressure is the selected characteristic.

Following process 400 where gauge pressure is the selected characteristic, at act 402, one or more current values of gauge pressure may be obtained. For example, the current value(s) for gauge pressure may be obtained by a pressure sensor disposed below the orifice plate 208, as shown in FIG. 2.

At act 404, a determination is made as to whether the current value for gauge pressure satisfies a compliance criterion. As dangerous conditions are created when pressure inside the gas extraction system is greater than atmospheric pressure, in some embodiments, satisfying the compliance criterion comprises the current value for gauge pressure being non-positive, or negative, and therefore indicating that the pressure inside the gas extraction system is not greater than atmospheric pressure. In other embodiments, it may be advantageous to maintain the pressure inside the gas extraction system at a predefined level below atmospheric pressure. Thus, in some embodiments, satisfying the compliance criterion for gauge pressure may include the current value for gauge pressure being less than or less than or equal to a negative value for gauge pressure. As described herein, acts 402 and 404 may be performed at predefined intervals, and for gauge pressure, may preferably be performed once a month.

When it is determined, at act 404, that the current value for gauge pressure satisfies the compliance criterion, the process 400 may return to act 402 to obtain an additional current value for gauge pressure, such that gauge pressure applied to the collection wellhead of the landfill gas extraction system is being continuously monitored, or the process 400 may end. When it is determined, at act 404, that the current value for gauge pressure does not satisfy the compliance criterion for gauge pressure, for example, when the current value for gauge pressure is positive, the process 400 proceeds to act 406 where a corrective action is performed. For gauge pressure, the corrective action preferably includes increasing flow rate of the extracted landfill gas by adjusting a flow control mechanism of the gas extraction system so as to decrease pressure inside the gas extraction system relative to atmospheric pressure.

Each of the acts described in process 400 may preferably be performed automatically in order to more efficiently remedy exceedances of selected characteristics. In some embodiments, however, the process 400 can be performed manually. In some embodiments, the process 400 can be performed automatically upon receiving an indication from a user, such as through a graphical user interface, as described herein. In addition, process 400 may include automated recording of data relating to the outcome of acts 402-406, as will be described further herein, to provide for compliance with regulations requiring recordation of landfill gas extraction operating conditions in a more efficient manner.

In some embodiments, the example process 400 for monitoring and controlling extraction of landfill gas from a landfill through a gas extraction system applies only to selected wells at a landfill site. For example, some wells at a landfill may not be designated for landfill gas extraction but rather are designated for odor control or gas migration, and some wells may be decommissioned, or covered by a geomembrane or synthetic cover which may mitigate or obviate the need for landfill gas extraction. In some embodiments, different compliance criteria may apply to different wells based on needs of the landfill and/or a plant receiving extracted landfill gas such that different wells are monitored and controlled in different ways. A graphical user interface may be provided for managing the different compliance criteria applicable to different wells, as described herein.

In some embodiments, the method 400 may proceed from act 406 as shown by the dashed line leading to act 408. The inventors have recognized that automatically performing a corrective action for a selected characteristic may cause other characteristics of the gas extraction process to result in an exceedance. For example, decreasing flow rate of extracted landfill gas to correct an exceedance in oxygen concentration of extracted landfill gas may cause increased pressure inside the gas extraction system such that a value for gauge pressure no longer satisfies a compliance criterion for gauge pressure. Thus, the subsequent acts following act 406 comprise additional actions subsequent to performing a corrective action to ensure that all of a group of selected characteristics satisfy their respective compliance criteria.

At act 408, in order to determine whether the corrective action performed in act 406 has created additional exceedances for additional characteristics of the landfill gas extraction process, a set of values is obtained after the corrective action has been performed including a subsequent value of the selected characteristic, and one or more values for at least one additional characteristic of the gas extraction process. For example, where the selected characteristic is oxygen concentration, a subsequent value for oxygen concentration is obtained at act 408 in addition to one or more values for at least one additional characteristic, for example, gas temperature and/or gauge pressure.

At act 410, it is determined whether the subsequent value for the selected characteristic and the value(s) for the additional characteristic(s) satisfy respective compliance criteria. For example, act 410 may comprise determining whether a subsequent value for oxygen concentration, the selected characteristic, satisfies a compliance criterion for oxygen concentration, and determining whether values for gauge pressure and gas temperature satisfy compliance criteria for gauge pressure and gas temperature, respectively. When it is determined, at act 410, that any one of the values obtained in act 408 fail to satisfy a respective compliance criterion, the process proceeds through the no branch to act 412, to perform a subsequent corrective action, including one or more of the corrective actions described herein, or an alternative corrective action. When it is determined, at act 410 that all of the values obtained in act 408 satisfy respective compliance criteria, the process 400 proceeds through the yes branch to act 402 where an additional current value for the selected characteristic is obtained, or alternatively, the process 400 may end.

As illustrated in FIG. 4, in some embodiments, the process 400 may continue past act 412 to obtain an additional set of values for the selected characteristic and additional characteristic(s), and may again determine whether the set of values satisfy the respective compliance criterion by returning to act 408. This process of taking measurements of multiple characteristics of the landfill gas extraction process in the same set of values may be repeated until no exceedances exist.

The inventors have further recognized that the processes described herein may be leveraged to monitor and maintain the health of various components of the gas extraction system. For example, the inventors have recognized that certain corrective actions for a selected characteristic should, if the gas extraction system is functioning properly, decrease the level of a characteristic which is determined to be at an exceedance. For example, when oxygen concentration is the selected characteristic, the corrective action may be decreasing flow rate of the extracted landfill gas through the gas extraction system. As described herein, decreasing flow rate should decrease the amount of oxygen in the extracted landfill gas and thus the oxygen concentration of extracted landfill gas should decrease. On the other hand, where gauge pressure is the selected characteristic, the corrective action may be increasing flow rate of the extracted landfill gas through the gas extraction system in order to decrease pressure within the gas extraction system. Gauge pressure is thus expected to decrease when the corrective action, increasing flow rate of the extracted landfill gas, is performed.

The inventors have recognized that comparing an expected outcome of the corrective action with an actual outcome of the corrective action by comparing initial (also referred to herein as a "current" value) and subsequent measurements of the selected characteristic can provide information of the health of the system. For example, when a corrective action is performed and the actual outcome does not match the expected outcome (i.e. where the subsequent value is not less than the current value where the corrective action is expected to decrease the selected characteristic), there is an indication that the gas extraction system is not functioning properly and one or more components of the gas extraction system may need to be repaired or replaced (e.g. one or more sensors, flow control mechanisms, or valves may be broken or there may be a leak in well piping, a hose, or elsewhere in the gas extraction system). Therefore, the process 400 may optionally proceed to act 411 after one or more subsequent values for the selected characteristic are obtained at act 408 after the corrective action is performed at act 406. At act 411, it is determined whether the subsequent value for the selected characteristic is less than the current value for the selected characteristic obtained at act 402.

If, act 411, it is determined that the subsequent value for the selected characteristic is less than the current value for the selected characteristic, the process 400 proceeds through the yes branch back to act 402 to obtain an additional current value for the selected characteristic. If, at act 411, it is determined that the subsequent value for the selected characteristic is not less than the current value for the selected characteristic, there is an indication that the gas extraction system is not functioning properly as the expected outcome of performing the corrective action does not match the actual outcome of performing the corrective action. The process 400 may then proceeds through the no branch at act 411 to act 412 to perform a subsequent corrective action. The subsequent corrective action may, in some embodiments, include notifying a user that one or more components of the gas extraction system may need to be repaired and/or replaced.

Although in the illustrated embodiment, the process 400 is explained in terms of a performing a corrective action which is expected to decrease the value of a selected characteristic, in some embodiments, the method 400 may be implemented with a corrective action which is expected to increase the value of a selected characteristic. For example, the compliance criterion may comprise the current value for the selected characteristic being above a lower threshold, and the corrective action may be performed to increase a value of the selected characteristic in response to a determination that the current value for the selected characteristic is less than the lower threshold. In that case, the determination made at act 411 may include determining whether the subsequent value for the selected characteristic is greater than the current value for the selected characteristic. If the subsequent value for the selected characteristic is not greater than the current value, performing the corrective action did not result in the expected outcome and a subsequent corrective action can be performed, for example, notifying a user that one or more components of the gas extraction system may need to be repaired and/or replaced. As should be appreciated from the foregoing, in some embodiments, act 411 may include determining whether a subsequent value for a selected characteristic is less than, less than or equal to, greater than, and/or greater than or equal to an current value for the selected characteristic.

In some embodiments, the process 400 may be adjusted such that the determination at act 404 is not required. For example, the example method for monitoring the health of components of a landfill gas extraction system may be used even where an exceedance for the selected characteristic is not detected. In such a process, an current value for a selected characteristic could be obtained and an action can be performed intended to increase or decrease the value of the selected characteristic. A subsequent value for the selected characteristic can be obtained and compared with the current value for the selected characteristic to determine whether the gas extraction system is functioning properly.

Figure 5:
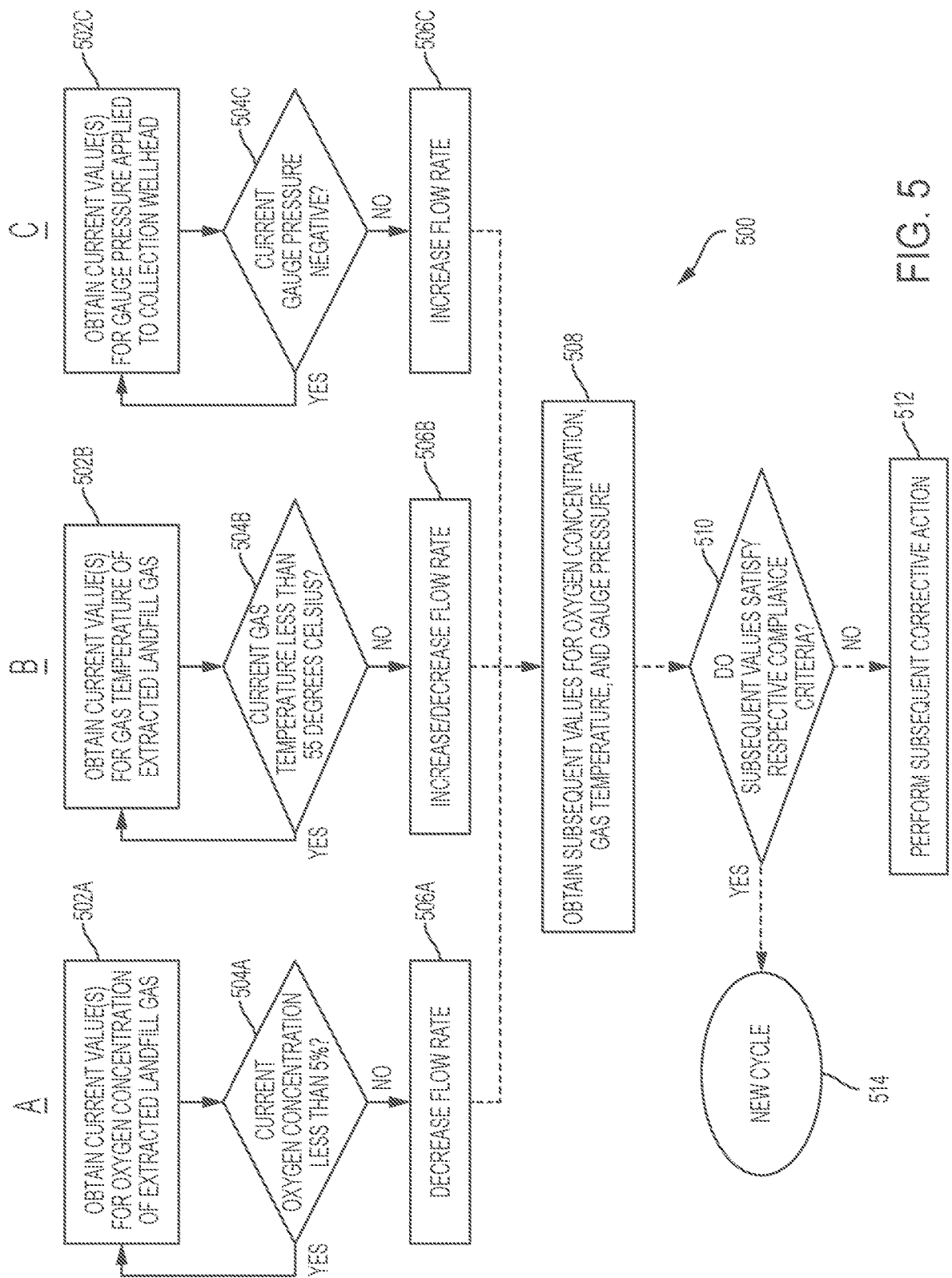
FIG. 5 is flowchart of another example method for controlling extraction of landfill gas from a landfill through a gas extraction system, in accordance with some embodiments of the technology described herein.

Various processes for monitoring and controlling the extraction of landfill gas have been described herein, including processes for different selected characteristics such as oxygen concentration, gas temperature, and gauge pressure. The inventors have appreciated that the processes described herein may be implemented individually, or may be performed approximately simultaneously and/or concurrently. For example, the gas extraction system can be configured to monitor multiple characteristics at once as shown in FIG. 5 where processes for monitoring and controlling landfill gas extraction based on oxygen concentration, gas temperature, and gauge pressure are performed approximately simultaneously. FIG. 5 is a flowchart of another example method for controlling extraction of landfill gas from a landfill through a gas extraction system, in accordance with some embodiments of the technology described herein.

According to the process 500, at acts 502A-C, current values for oxygen concentration, gas temperature, and gauge pressure are obtained. In some embodiments, acts 502A-C may be performed at approximately the same time and at approximately the same frequency. However, the inventors have recognized that it is advantageous to sample certain characteristics of the landfill gas process more often than others in order to ensure safety of the gas extraction process and optimal methane extraction. For example, measurements of oxygen concentration of extracted landfill gas may be obtained more frequently than either of gas temperature and gauge pressure. In some embodiments, measurements of oxygen concentration of extracted landfill gas may be obtained at least once per day, and measurements of gas temperature and gauge pressure may be performed at least once per month.

At acts 504A-C, current values for oxygen concentration, gas temperature, and gauge pressure are monitored to determine whether the current values for each characteristics satisfy a respective compliance criterion. For example, in the illustrated embodiment, act 504A determines whether the current value for oxygen concentration is less than 5%, act 504B determines whether the current value for gas temperature is less than 55 degrees Celsius, and act 504C determines whether the current value for gauge pressure is negative. Although the illustrated embodiment in FIG. 5 illustrates specific compliance criteria at acts 504A-C, any of the compliance criteria described herein could be used at acts 504A-C.

If, at acts 504A-C, the answer is yes, the process 500 proceeds through the yes branch to obtain another current value for the selected characteristic, or alternatively, ends. If, at acts 504A-C, the answer is no for any of acts 504A-C, the process proceeds to acts 506A-C, depending on which of the selected characteristics resulted in an exceedance. At acts 506A-C, a corrective action corresponding to the selected characteristic which resulted in an exceedance is performed, for example, increasing or decreasing a flow rate of extracted landfill gas through the gas extraction system. Although the illustrated embodiment in FIG. 5 illustrates specific corrective actions, any of the corrective actions described herein could be used at acts 506A-C.

In some embodiments, the process 500 may optionally proceed from any of acts 506A-C to act 508 where a set of values including oxygen concentration, gas temperature and gauge pressure are obtained. The inventors have recognized that it is advantageous to obtain a set of measurements including oxygen concentration, gas temperature, and gauge pressure after performing a corrective action, to ensure that a corrective action intended to address an exceedance for a selected characteristic does not create an exceedance for another characteristic.

At act 510, it may be determined whether each value in the set of subsequent values satisfy a respective compliance criterion. The respective compliance criterion may be the same compliance criterion that was used at acts 504A-C, or the compliance criterion may be different.

If, at act 510, any of the subsequent values fail to satisfy a respective compliance criterion, the process 500 may proceed through the no branch to act 512, where a subsequent corrective action is performed. The subsequent corrective action may be any of the corrective actions described herein. In some embodiments, the subsequent corrective action may include continuing to monitor values for the selected characteristics by obtaining an additional set of subsequent values including a value for each of the selected characteristics. If, however, at act 510 all of the subsequent values are determined to satisfy a respective compliance criterion, the process 500 may proceed through the yes branch to act 514, where a new cycle of the process 500 is performed, or alternatively, the process 500 may end.

FIG. 5 illustrates that selected characteristics of the landfill gas extraction process, including oxygen concentration, gas temperature, and gauge pressure may be monitored at substantially the same time. However, in some embodiments, acts in the A, B, and C branches of process 500 may not be performed simultaneously. For example, act 502A may not necessarily be performed at the same time as acts 502B-C.

Although in the illustrated embodiment, the process 500 is configured to monitor and control landfill gas extraction based on measurements of oxygen concentration, gas temperature, and gauge pressure, in some embodiments, one or more other characteristics of the landfill gas extraction process may additionally or alternatively be monitored using the process 500.

In some embodiments, the methods described herein for controlling extraction of landfill gas extraction may be continuously performed, while in other embodiments, the methods may be performed only for certain intervals, such as during intervals of active or increased extraction of landfill gas (e.g., during the day, during the night, etc.). In some embodiments, detecting an exceedance (i.e. when a value for a selected characteristic fails to satisfy a compliance criterion) may necessitate being corrected within a certain time frame (e.g., twenty-four hours), and when the exceedance has not been corrected within the time frame, a subsequent corrective action may be taken (e.g., a manual operation, notifying a governing body, etc.).

Figure 6:
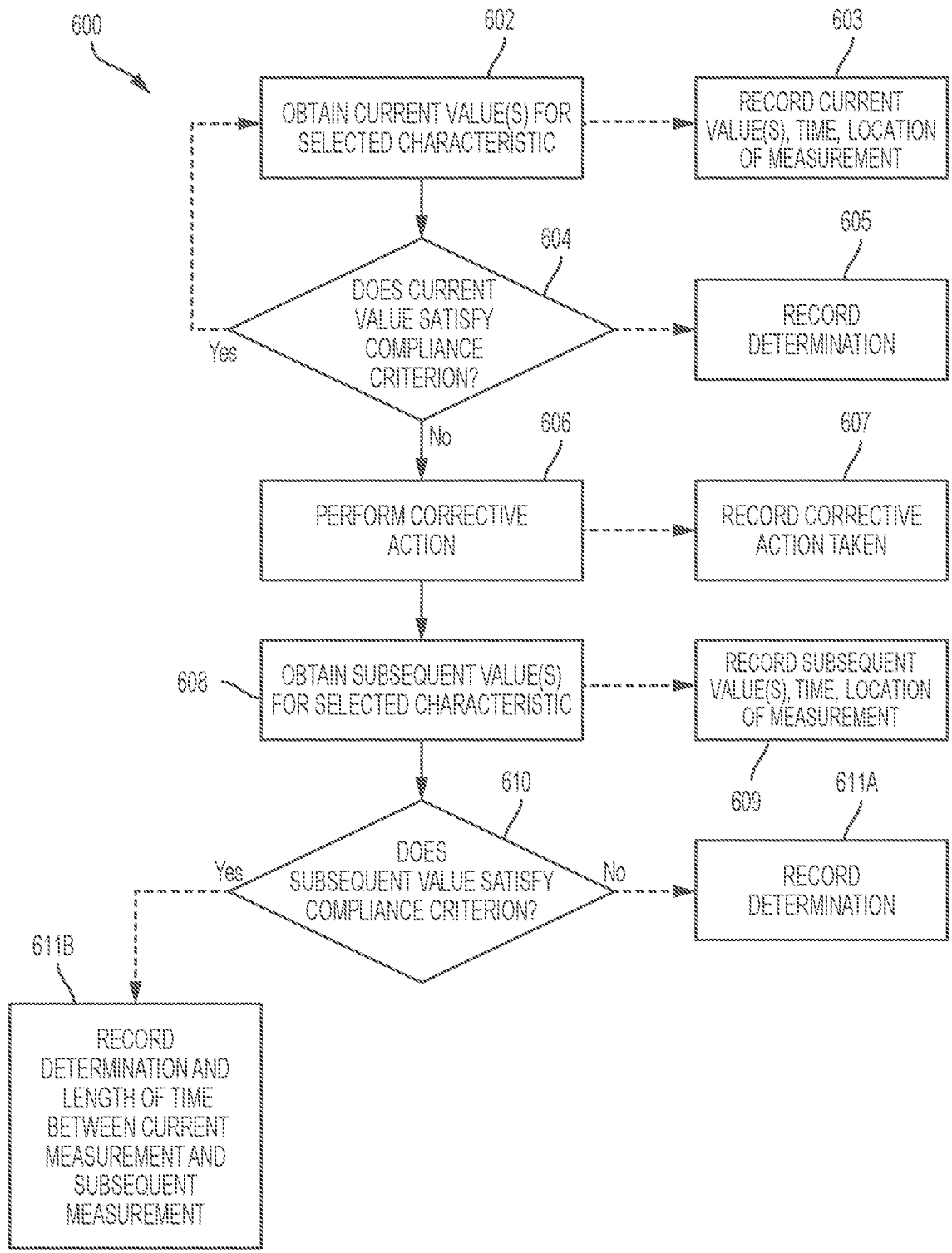
FIG. 6 is a flowchart of another example method for controlling extraction of landfill gas from a landfill through a gas extraction system, in accordance with some embodiments of the technology described herein.

The methods and systems described herein may also provide for automatic documentation of landfill gas extraction data. FIG. 6 is a flowchart of an example method for monitoring extraction of landfill gas from a landfill through a gas extraction system, in accordance with some embodiments of the technology described herein illustrating automatic recording of landfill gas extraction data.

FIG. 6 illustrates that the processes described herein can be implemented with automatic data recording. For example, process 600 may begin at act 602 where one or more current values for a selected characteristic are obtained. Block 603 illustrates that the current value obtained at act 602, the time the current value was obtained, and/or the location of the sensor and/or well the current value was obtained from may be automatically recorded in act 603 in a system memory.

At act 604, it is determined whether the current value for the selected characteristic satisfies a compliance criterion for the selected characteristic. The compliance criterion in act 606 may be any of the compliance criteria described herein, or any other suitable compliance criterion. If, at act 604, it is determined that the current value does satisfy the compliance criterion, the process may return through the yes branch to act 602 where an additional current value for a selected characteristic is obtained. In some embodiments, an indication that the current value for the selected characteristic was determined to satisfy the compliance criterion is stored in system memory. If, at act 604, it is determined that the current value does not satisfy the compliance criterion, the process 600 may proceed through the no branch to act 606. Block 605 illustrates that the determination made at act 604 as to whether the current value satisfies the compliance criterion may be automatically recorded and stored in system memory. For example, at act 605, the current value recorded at act 603 may be marked as an exceedance.

At act 606, a corrective action for the selected characteristic is performed. The corrective action may be any of the corrective actions described herein, or any other suitable corrective action for the selected characteristic. Block 607 illustrates that the corrective action taken may be automatically recorded and stored in system memory. For example, where the corrective action is adjusting a flow rate of extracted landfill gas, act 607 may include automatically recording an indication that flow rate of extracted landfill gas was adjusted, how flow rate was adjusted (e.g., increased or decreased), the increment in which flow rate was adjusted (e.g. a change in position of a valve of a flow control mechanism), the time of the adjustment, the location of the adjustment, and/or any other suitable information related to performing the corrective action.

At act 608, a subsequent value for the selected characteristic is obtained. At block 609, the subsequent value obtained at act 608, the time the subsequent value was obtained, and/or the location of the sensor and/or well the subsequent value was obtained from may be automatically recorded in act 609 and stored in system memory.

The process 600 may proceed to act 610 where it is determined whether the subsequent value satisfies a compliance criterion for the selected characteristic. The compliance criterion in act 610 may be any of the compliance criteria described herein, or any other suitable compliance criterion. In some embodiments, the compliance criterion in act 610 is the same as the compliance criterion in act 606, and in other embodiments, a different compliance criterion may be used in act 610 than the compliance criterion used in act 606.

If, at act 610, the subsequent value is determined not to satisfy the compliance criterion, the process 600 may optionally proceed through the no branch to act 611A where the determination that the subsequent value does not satisfy the compliance criterion is automatically recorded into system memory. If, at act 610, it is determined that the subsequent value does satisfy the compliance criterion, the process 600 may optionally proceed through the yes branch to act 611B where the determination that the subsequent value does satisfy the compliance criterion is automatically recorded into system memory. At act 611B, a length of time between the initial measurement of the current value and the subsequent measurement of the subsequent value may also be recorded, to determine the length of time that the selected characteristic exceeded a threshold value (by failing to satisfy the compliance criterion). Although not shown in FIG. 6, when it is determined, at act 610, that the subsequent value does not satisfy the compliance criterion, the process 600 may return to one or more preceding acts, such as act 606, where a corrective action is performed.

In some embodiments, the process 600 may also include determining a length of time between the time at which an exceedance for a characteristic of the landfill gas extraction process is first detected (e.g., the time when it is determined that a value of a selected characteristic does not satisfy a respective compliance criteria) and the time at which no exceedances exist for any of a number of monitored characteristics of the landfill gas extraction process. For example, in some embodiments, the system may be configured to monitor oxygen concentration, gas temperature, and gauge pressure, and a length of time during which any of these parameters are at an exceedance may be determined and recorded in a database. In some embodiments, at least one controller of the system may be configured to record all measurements of the monitored landfill gas extraction characteristics and any corrective actions performed in a database for the length of time during which the system is experiencing at least one exceedance.

In some embodiments, the system may be configured to return to an "initial" or "normal" mode of operations when there are no exceedances of monitored characteristics. For example, at least one controller of the system may be configured to determine when any exceedances of monitored characteristics of the landfill gas extraction process have been corrected, and thereafter instruct the system to return to an initial mode of operation. The initial mode of operation may comprise monitoring landfill gas extraction characteristics at less frequent intervals, for example, obtaining measurements of oxygen concentration at least once per week and measurements of gas temperature and/or gauge pressure at least once per month. In some embodiments, an initial mode of operation may comprise obtaining measurements for monitored parameters individually, as opposed to at substantially the same time.

The process 600 may be implemented for any of the selected characteristics described herein, or any other suitable characteristic of the landfill gas extraction process. In some embodiments, the process 600 may be implemented for multiple characteristics at the same time, concurrently or otherwise.

In some embodiments, automated methods of recording landfill gas extraction measurements may include automatically generating a report having values for one or more selected parameters. For example, in some embodiments, at least one controller of a landfill gas extraction system may be configured to automatically generate a report on a predefined basis (e.g., hourly, daily, weekly, monthly, yearly, etc.) including values for one or more parameters of the landfill gas extraction process such as number of exceedances in total and/or for a selected characteristic, values for reported exceedances, location of exceedances, time of exceedances, duration of exceedances, identified cause of the exceedance, corrective action taken, and/or time the exceedance was corrected. In some embodiments the automatically generated report may include additional information such as a description and duration of any interval in which the landfill gas flow is diverted from an In Situ Control Mechanism, as described herein, a description and duration of any interval in which the In Situ Control Mechanism was not operating for periods exceeding one hour, a description and duration of any interval in which the landfill gas extraction system was not operating for periods exceeding five days, and/or the date of installation and location of each well or landfill gas extraction system to date or within a particular time interval (e.g. within the last week, month, year, etc.).

As described herein, the automatically generated report may include information related to exceedances of characteristics of the landfill gas extraction process. In some embodiments, the automatically generated report may include information related to exceedances of methane concentration, for example, the location of any exceedance of methane concentration above 500 parts per million, and the value of methane concentration at that location. In some embodiments, the automatically generated report may include values for selected characteristics, such as methane or any other characteristics described herein, which previously reported an exceedance within a particular time frame (e.g., within the last week, month, year, etc.).

In some embodiments, the automatically generated report includes all collected data for one or more selected characteristics of the landfill gas extraction process, while in others, the automatically generated report includes only data related to locations and selected characteristics which resulted in an exceedance. In some embodiments, the automatically generated report includes exceedance information (e.g., number of exceedances in total and/or for a selected characteristic, as described herein, values for reported exceedances, location of exceedances including location of a sensor and/or well, time of exceedances, duration of exceedances, corrective action taken, etc.) and subsequent information for the location that reported an exceedance for a subsequent time interval (e.g., in the next day, week, month, year, etc.) including a value for one or more characteristics of the landfill gas extraction process (e.g., oxygen concentration, temperature, gauge pressure, methane concentration, or any other characteristics of the gas extraction process described herein or any other suitable characteristic), a determination as to whether or not the subsequent value is an exceedance, and the location of the exceedance.

In some embodiments, a data store of the gas extraction system may be configured to store data collected from the gas extraction system for a predefined time interval (e.g., at least one year, at least five years, etc.).

Although methods have been described herein with respect to automatically recording data collected from a landfill gas extraction system and automatically generating a report of the collected data, in some embodiments, the report can additionally or alternatively be generated upon a user command. For example, a user may request generation of a report of collected data from a landfill gas extraction system using a GUI, for example using an export button provided on a GUI.

Figure 7:
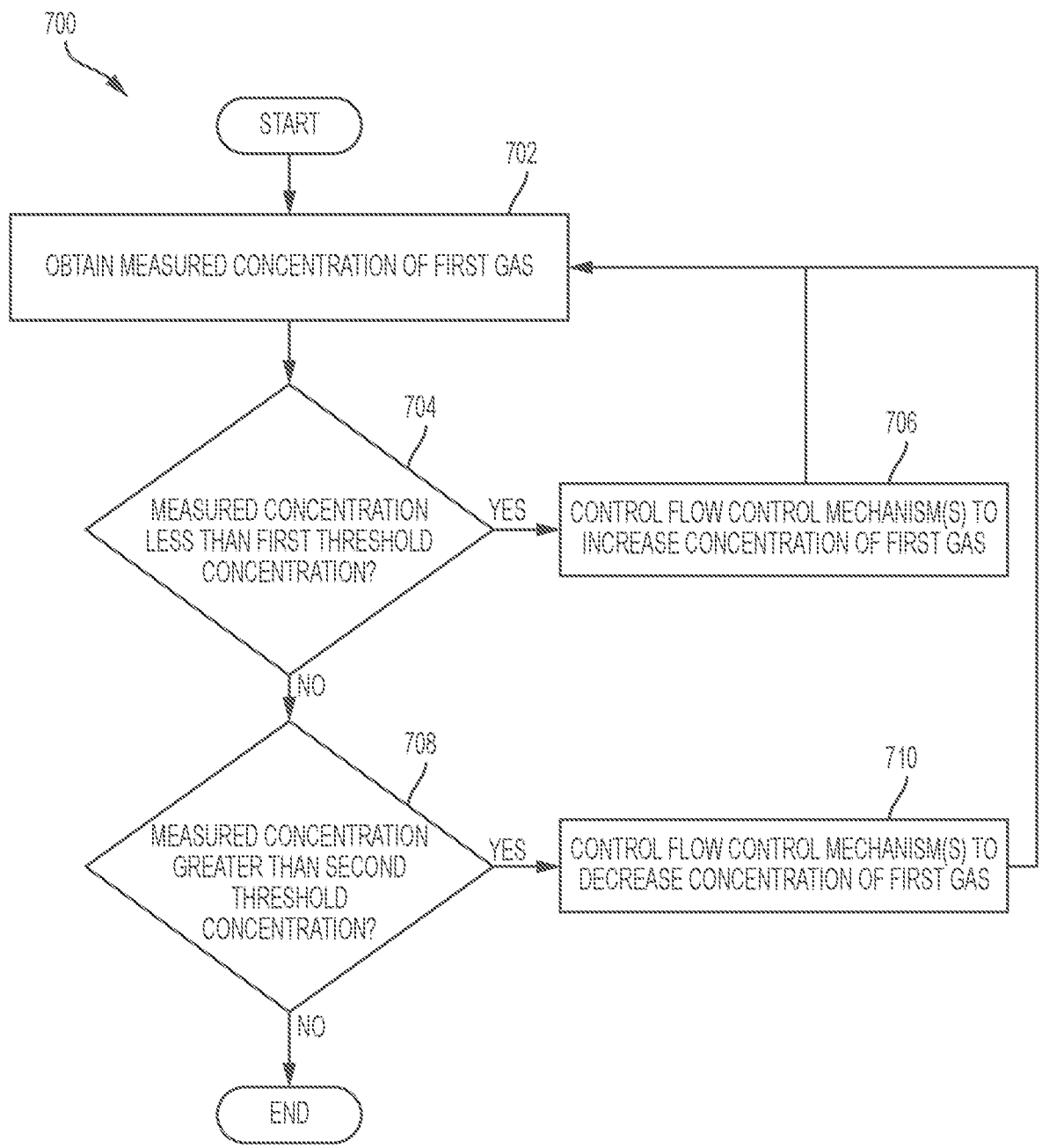
FIG. 7 is a flowchart of another example method for monitoring extraction of landfill gas from a landfill through a gas extraction system, in accordance with some embodiments of the technology described herein.

The inventors have appreciated that the methods described herein for automated compliance of landfill gas extraction may be performed in conjunction with control methods for optimizing the methane content of extracted landfill gas to ensure safe and high quality landfill gas extraction. For example, FIG. 7 is a flowchart of an example method for monitoring extraction of landfill gas from a landfill through a gas extraction system, in accordance with some embodiments of the technology described herein.

Method 700 begins at act 702 where a measured concentration of a first gas, for example, methane, is obtained. At act 704, it is determined whether the measured concentration of the first gas obtained at act 702 is less than a first threshold concentration.

If, at act 704, it is determined that the measured concentration of the first gas is less than a first threshold concentration, the method 700 may proceed through the yes branch to act 706 to control one or more flow control mechanisms to increase concentration of the first gas. The method 700 may then proceed back to act 702 where a measured concentration of the first gas is obtained. If, at act 704, it is determined that the measured concentration of the first gas is not less than a first threshold concentration, the method 700 may proceed through the no branch to act 708, where it is determined whether the measured concentration of the first gas is greater than a second threshold concentration.

If, at act 708, it is determined that the measured concentration of the first gas is greater than a second threshold concentration, the method 700 may proceed through the yes branch to act 710 to control one or more flow control mechanisms to decrease concentration of the first gas. The method 700 may then proceed back to act 702 where a measured concentration of the first gas is obtained. If, at act 708, it is determined that the measured concentration of the first gas is not greater than the second threshold concentration, the method 700 may proceed through the no branch to an end.

In some embodiments, the first gas is methane, the first threshold concentration is 45% methane and the second threshold concentration is 55% methane. In some embodiments, the first threshold concentration is 55% methane and the second threshold concentration is 65% methane. In some embodiments, landfill gas extraction is additionally or alternatively controlled based on aggregate gas composition and flow data from a plant receiving landfill gas extracted from the landfill. In some embodiments, the method 700 is performed at discrete time intervals (e.g. hourly, daily, weekly, monthly, etc.).

Although the method 700 is described herein with respect to methane concentration, the inventors have recognized that the method 700 may be used with any suitable constituent gas (e.g. $CO_2$, $O_2$, $N_2$, etc.) to optimize the quality of extracted landfill gas. In addition, although the optimization method 700 is related to measuring and comparing concentrations of extracted landfill gas, the compliance methods described herein may be implemented with any suitable control method for optimizing the quality of extracted landfill gas, such as the methods described in U.S. Pat. No. 10,029,290, titled "Devices and Techniques Relating to Landfill Gas Extraction", filed on Nov. 4, 2014, which is hereby incorporated by reference herein in its entirety and U.S. patent application Ser. No. 15/493,174, titled "Devices and Techniques Relating to Landfill Gas Extraction", filed on Aug. 3, 2017, which is hereby incorporated by reference herein in its entirety.

Figure 8:
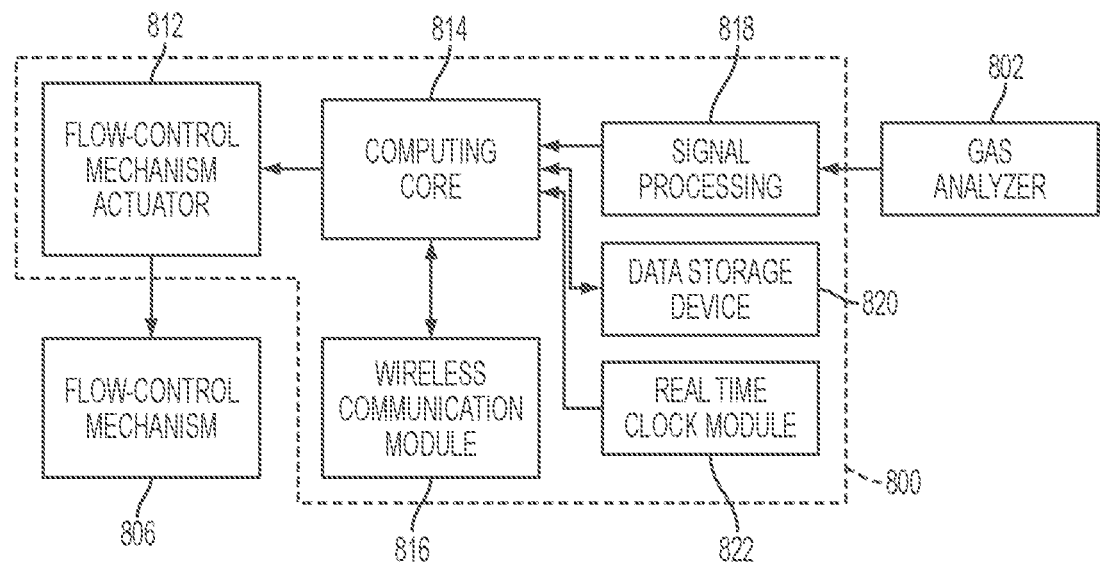
FIG. 8 is a block diagram of a control mechanism of the example gas extraction system of FIG. 1, in accordance with some embodiments of the technology described herein.

In some embodiments, the methods described herein are performed by at least one controller of the gas extraction system. FIG. 8 is a block diagram of a control mechanism of the example gas extraction system of FIG. 1, in accordance with some embodiments of the technology described herein. In some embodiments, the Controller 800 of an In Situ Control Mechanism may include functional blocks as indicated in FIG. 8. In the embodiment of FIG. 8, the Controller 800 includes a Signal Processing Module 818, a Data Storage Device 820, a Real Time Clock Module 822, a Wireless Communication Module 816, and/or a Flow control Mechanism Actuator 812 (e.g., valve drive buffer) for providing a control signal to the Flow control Mechanism 806. Other embodiments may use only parts of this implementation, while others may add additional functional modules for supporting functions. For example, in some embodiments, the Controller of an In Situ Control Mechanism may be implemented using a one or more processors as described below.

In some embodiments, the Controller 800 of the In Situ Control Mechanism may further use data about environmental conditions in and around the landfill (e.g., in and around the gas extraction well upon which the In Situ Control Mechanism is installed) to determine the settings to be applied to the flow control mechanism. In some embodiments, a remotely-located controller may use the environmental data to determine the settings to be applied to the flow control mechanism, and may communicate those settings to the In Situ Control Mechanism. The environmental data may include information about parameters including, but not limited to atmospheric pressure, ambient temperature, wind direction, wind speed, precipitation, and/or any other suitable environmental parameter. The In Situ Control Mechanism may use information from other sensors placed in or around the gas extraction well, including, without limitation, subsurface temperature probes, subsurface moisture probes, measurements of the chemical and/or biological processes (for example, pH measurements, tests for the presence of other chemicals or biological by-products, etc.) occurring in the section of waste that is in the vicinity of the gas extraction well, and/or any other suitable information.

In some embodiments, the Signal Processing Module 818 takes gas characteristics data from the Gas Analyzer 802 and converts it into a form that can be interpreted by the Computing Core 814. This may involve a interpreting a serial digital data stream via a serial parsing algorithm, a parallel parsing algorithm, analog signal processing (for example, performing functions on analog signals like filtering, adding or removing gain, frequency shifting, adding or removing offsets, mixing or modulating, and the like), digital signal processing (digital filtering, convolution, frequency shifting, mixing, modulating, and the like), analog-to-digital or digital-to analog conversion, and/or any other suitable signal processing technique that will be recognized by one of ordinary skill in the art.

In some embodiments, the Data Storage Device 820 may include any volatile and/or non-volatile memory element, including but not limited to flash memory, SD card, micro SD card, USB drive, SRAM, DRAM, RDRAM, disk drive, cassette drive, floppy disk, cloud storage backup, and/or any other suitable computer-readable storage medium. The Data Storage Device may serve as a data recovery backup, or it may hold data for temporary intervals during the calculation of control signals. The Data Storage Device may be removable, or it may be fixed.

In some embodiments, the Real Time Clock Module 822 may include any circuit and/or functional module that allows the Computing Core to associate the results of a Gas Analyzer reading with a date or time (e.g., a unique date or time stamp).

In some embodiments, the Wireless Communication Module 816 may include, but is not limited to: a radio transceiver (AM or FM, or any other type), television, UHF, or VHF transceiver, Wi-Fi and/or other 2.4 GHz communication module, cellular chipset (2G, 3G, 4G, LTE, GSM, CDMA, etc.), GPS transmitter, satellite communication system, and/or any other suitable wireless communication device. The Wireless Communication Module may have an integrated antenna, and/or an external one. The Wireless Communication Module may transmit, receive, and/or have two-way communication with a central source and/or be capable of point-to-point communication with another module. In some embodiments, the Wireless Communication Module may include a 2G chipset that allows the In Situ Control Mechanism to connect to existing telecommunications infrastructure.

In some embodiments, the Computing Core 814 may include, but is not limited to: a microprocessor, a computer, a microcontroller, a field programmable gate array (FPGA), an application specific integrated circuit (ASIC), a digital signal processor (DSP), an analog computer or control system, and/or any other suitable computing device. In some embodiments, the Computing Core may have integrated Analog-to-Digital converters, pulse width modulation detectors, edge detectors, frequency detectors, phase detectors, amplitude detectors, demodulators, RMS-DC converters, rectifiers, and/or other suitable signal processing modules.

In some embodiments, the Flow control Mechanism Actuator 812 (e.g., a valve drive buffer) may include any circuit that can translate commands from the Computing Core into an appropriate actuation signal (e.g., driving signal) for the Flow control Mechanism 806. In some embodiments, translating commands from the Computing Core may comprise analog signal processing on a voltage (for example, adding/removing gain, offset, filtering, mixing, etc.), analog signal processing on a current control (for example, conversion to a 4-20 mA control loop, increasing output current drive capability), pulse width modulating a digital signal, digital signal processing, digital-to-analog or analog-to-digital conversion, and/or any other suitable techniques.

In some embodiments, some or all of the gas extraction wells and/or piping junction points in a landfill may be outfitted with In-Situ Control Mechanisms to form at least a portion of a control system for controlling gas extraction across the entire landfill or a set of wells within the landfill (the "landfill under control"). FIG. 9 is a block diagram of an example control system for controlling extraction of landfill gas from a landfill through a gas extraction system, in accordance with some embodiments of the technology described herein.

FIG. 9 shows a control system 900 for a landfill gas extraction system, according to some embodiments. In some embodiments, control system 900 may include one or more In Situ Control Mechanisms 906 configured to control gas flow in a gas extraction system in a landfill under control 920. In some embodiments, control system 900 may include a controller module 904 for modeling aspects of the landfill under control, for communicating with the In Situ Control Mechanisms, and/or for controlling the operation of the In Situ Control Mechanisms. In some embodiments, controller module 904 may be implemented on one or more computers located remotely from the In Situ Control Mechanisms (e.g., on a centralized computer or in a distributed computing environment). In some embodiments, controller module 904 may execute a multitasking program with different tasks configured to control the operation of different In Situ Control Mechanisms and/or to communicate with different In Situ Control Mechanisms. In some embodiments, the functionality described below as being performed by controller module 904 may be performed by one or more In Situ Control Mechanisms 906 individually or in concert. In some embodiments, controller module 904 may communicate with the In Situ Control Mechanisms through a device manager 902. In some embodiments, controller module 904 be in communication with a user interface 908 and/or a database 910.

In some embodiments, some or all of these In-Situ Control Mechanisms 906 may contain wireless communication capability to establish Wireless Data Links to controller module 904 (e.g., through device manager 502). Wireless Data Links may operate in either a unidirectional or a bidirectional manner. The network of Wireless Data Links may be implemented using a mesh network, a star network, point-to-point communication, and/or any other suitable communication technique. In-Situ Control Mechanisms 906 may send information over a communication network to a distributed network (e.g., the "cloud"). Communication may occur through a system including but not limited to a cell phone network (2G, 3G, 4G LTE, GSM, CDMA 1×RTT, etc.), a satellite network, a local area network connected to the Internet, etc. In some embodiments, the In Situ Control Mechanisms 906 may communicate with each other and/or with controller module 904 using wired data links, Wireless Data Links, power line communication, and/or any other suitable communication technique.

Information sent (e.g., over Wireless Data Links) by the In-Situ Control Mechanisms 906 may include but is not limited to sensor data, environmental data, failure notifications, status notifications, calibration notifications, etc. Information received by the In-Situ Control Mechanisms may include but is not limited to: raw or pre-processed data about the current or past operational state of other landfill gas extraction wells in the landfill under control, command and control signals, desired operating states, predictive calculations about the operating state of the well upon which the In-Situ Control Mechanism is installed or other landfill gas extraction wells, failure notifications, status notifications, calibration changes, software and/or firmware updates, flow control mechanism settings, sensor settings, and/or other information.

In some embodiments, In Situ Control Mechanisms 906 in the landfill under control 920 may communicate with a Device Manager 902, as indicated in FIG. 9, and/or they may communicate directly with each other. The Device Manager 902 may include software operating on a computer in the landfill under control, or operating on a remote server, and/or operating on a distributed computing network ("the cloud") in one or multiple locations. In some embodiments, Device Manager 902 may be implemented using a computing system 1800 as described below. The Device Manager 902 may collect information from alternate sources—including but not limited to environmental data, past history about electrical power demand and/or prices, forecasts about future electrical power demand and/or prices, etc. In some embodiments, the Device Manager 902 may be in constant communication with the In-Situ Control Mechanisms 906, or it may communicate asynchronously with the In-Situ Control Mechanisms. In some embodiments, the Device Manager 902 may hold a queue of commands or other information to be passed to the In Situ Control Mechanism (s) 906 upon the establishment of a data link (e.g., re-establishment of a Wireless Data Link).

In some embodiments, the Device Manager 902 may associate a set of In-Situ Control Mechanisms 906 into a single landfill under control 920, and it may add or remove additional In-Situ Control Mechanisms 906 to that landfill under control 920 to accommodate the addition or removal of In-Situ Control Mechanisms from the site. The Device Manager 902 may contain or perform authentication or encryption procedures upon establishing a data link (e.g., a Wireless Data Link) with an In-Situ Control Mechanism. Security protocols implemented by the Device Manager may include, but are not limited to: internet key exchange, IPsec, Kerberos, point to point protocols, transport layer security (TLS), HTTPS, SSH, SHTP, etc.

In some embodiments, the Device Manager 902 may communicate with a controller module 904. The controller module 904 may include one or more applications running on a distributed computational platform (e.g., a "cloud server"), a traditional server infrastructure, a computing system 1800 as described below, and/or other suitable computer architecture recognized by those of ordinary skill in the art. It should be appreciated, however, that control functions as described herein may be distributed across device manager 902, controller module 904 and/or any other computing components in any suitable way. Similarly, control functions may be distributed across processors (e.g., controllers) associated with one or more In Situ Control Mechanisms.

Figure 10:
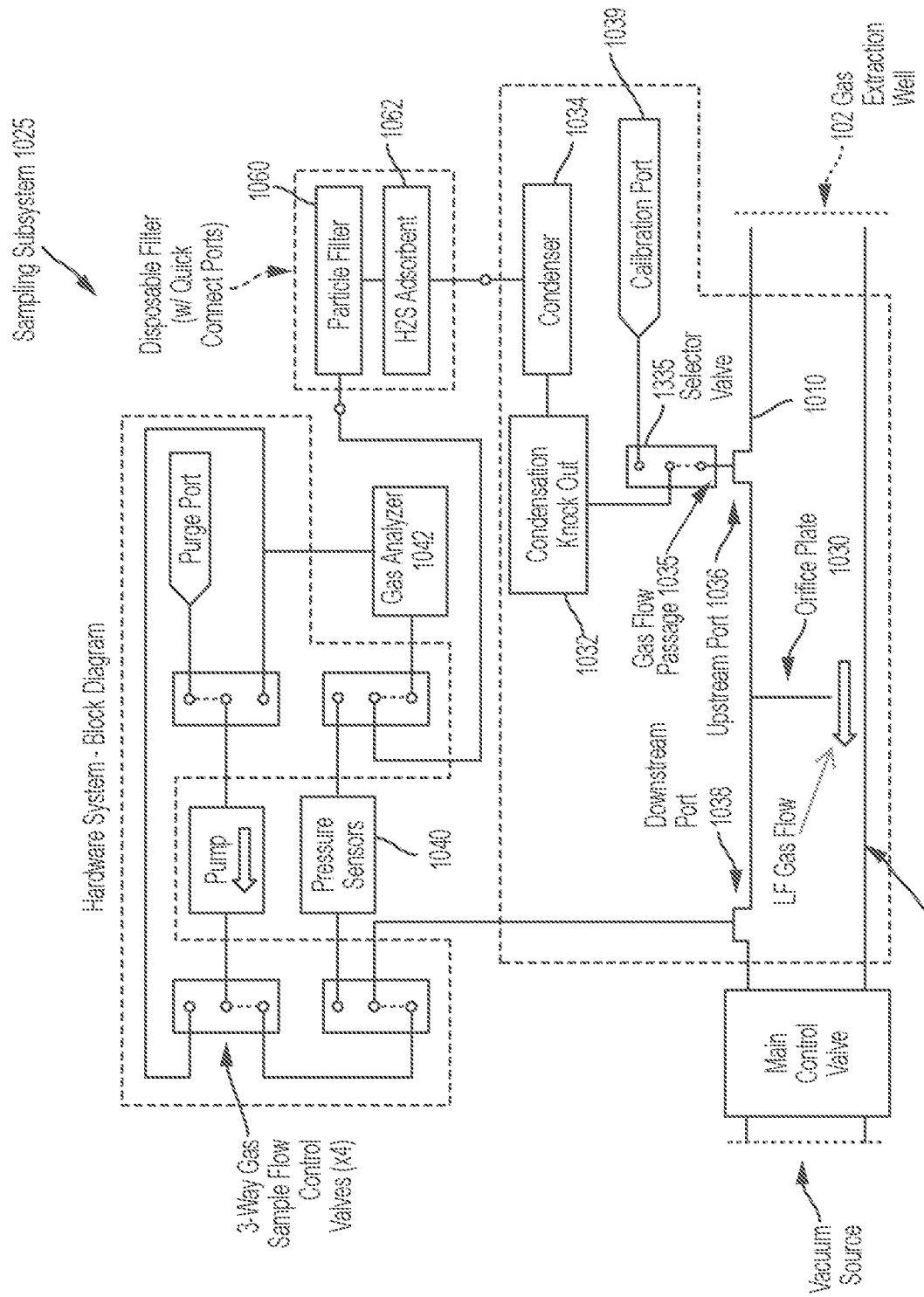
FIG. 10 is a block diagram of an example landfill gas extraction system, in accordance with some embodiments of the technology described herein.

As described herein, the gas extraction system may include various pretreatment mechanisms installed in the flow of the landfill gas stream to increase the longevity of the gas extraction system and its components. Furthermore, calibration of one or more sensors of the gas extraction system may improve the accuracy of measurements made by the one or more sensors. FIG. 10 is a block diagram of an example landfill gas extraction system having pretreatment mechanisms and a calibration port, in accordance with some embodiments of the technology described herein.

As shown in FIG. 10, in some embodiments, a section 1015 of a landfill gas extraction pipe 1010 is coupled to a sampling subsystem 1025 of a gas extraction system, including an upstream port 1036 and a downstream port 1038. Landfill gas may be configured to flow from a gas extraction well 102 through the section 1015 of the pipe 1010, and in some embodiments may be diverted through the upstream port 1036 along a gas flow passage 1035, and may reenter the pipe 1010 through the downstream port 1038 after passing through various components of the sampling subsystem 1025. An orifice plate 1030 may be coupled to the section 1015 of the pipe 1010 and configured to measure flow rate of extracted landfill gas.

One or more components may be coupled to the gas flow passage 1035 to condition gas before the gas is exposed to a sensor. Such conditioning may reduce damage to the sensor caused by the harmful characteristics of the landfill gas. For example, the gas flow passage may have at least one fluid knock-out 1032, which may aid in removing moisture from the landfill gas. In some embodiments, the gas flow passage 1035 may pass adjacent to and may be in thermal contact with a condenser 1034 configured to separate at least one undesired element (for example, moisture) from the landfill gas. In some embodiments the gas flow passage 1035 includes an adsorbent 1062 configured to scrub hydrogen sulfide ($H_2S$) or other contaminants from the sample gas. In some embodiments, the gas flow passage 1035 includes one or more filters, such as a particle filter 1060 for at least one of a particulate and/or a corrosive gas. Although FIG. 10 illustrates one embodiment of a sampling subsystem having pretreatment mechanisms, the order of the pre-treatment mechanisms disposed along the gas flow passage 1035 may be varied. In some embodiments, it may be advantageous to additionally or alternatively condition the gas using the one or more pre-treatment mechanisms described herein after the extracted landfill gas passes by one or more sensors along the gas flow passage 1035.

In some embodiments, the sampling subsystem 1025 may include a sample chamber 1042 as described herein, having one or more sensors for measuring characteristics of extracted landfill gas. The sampling subsystem 1025 may further include additional sensors 1040 along the gas flow passage 1035 and external to the sample chamber 1042.

The sampling subsystem 1025 may be coupled to at least one selector valve 1335 that diverts the sample path from the landfill gas stream flowing through the pipe 1010 to a calibration port 1039 coupled a calibration medium. The valve 1335 may be connected between the calibration port 1039 and a sensor, so as to enable gas to flow from the calibration port to the sensor. The valve 1335 may be actuated manually, automatically based upon a predefined schedule, remotely, and/or in response to a selected operation, for example by the detection of a fitting being connected to the calibration port 1039.

The inventors have recognized that in order to improve the monitoring and control processes described herein, the one or more sensors of the gas extraction system should be calibrated to ensure accurate measurements. A calibration medium of known composition coupled to the calibration port 1039 may be used to calibrate one or more sensors of the gas extraction system. The gas extraction system may be configured to execute various calibration methods for calibrating the one or more sensors of the gas extraction system.

In some embodiments, calibration of one or more sensors may be performed twice using the same calibration medium to ensure accuracy of the calibration. In some embodiments, the calibration medium comprises a first gas of known composition and a second gas of known composition, wherein the first gas of known composition is different from the second gas of known composition. In some embodiments, the first gas comprises oxygen while the second gas does not comprise oxygen. In some embodiments, the first gas comprises methane while the second gas does not comprise methane. In some embodiments, at least one of the first and second gasses comprise 35% $CO_2$, 50% $CH_4$, 15% $N_2$, and 0% $O_2$. In some embodiments, at least one of the first and second gasses comprises ambient air. In some embodiments, at least one of the first and second gasses comprises approximately 10-12% $O_2$, or any value on or within that range (e.g. 11% $O_2$).

As described herein, calibration of the one or more sensors of the gas extraction system can be performed manually or in response to a user indication. In other embodiments, calibration is automatic, and may be performed at predefined intervals (e.g. hourly, daily, weekly, monthly, etc.). Such predefined intervals can be defined by a user through a graphical user interface, as described herein. The manner and interval at which a sensor is calibrated may depend on the type or location of the sensor being calibrated. For example, in some embodiments, sensors for measuring gas composition can be calibrated more frequently, for example, once a week, than sensors for measuring other characteristics of the landfill gas extraction process, which can be calibrated once a month, for example.

In some embodiments, the one or more sensors may be calibrated before obtaining at least one measurement of a characteristic of the landfill gas extraction process. In some embodiments, the one or more sensors may be calibrated after performing a corrective action and prior to obtaining an additional measurement by the one or more sensors of a characteristic of the landfill gas extraction process.

In some embodiments, calibration of one or more sensors may be performed in response to the occurrence of a condition. For example, calibration may be automatically performed in response to obtaining a measurement that exceeds a particular threshold which may suggest the sensor is not functioning appropriately. In some embodiments, calibration may be performed automatically when any of one or more characteristics monitored by the system experience an exceedance (e.g., when oxygen concentration is greater than or equal to 5%, when gas temperature is greater than or equal to 55 degrees Celsius, and/or when gauge pressure is non-negative).

The gas extraction system may be configured to automatically record data related to a calibration of one or more sensors of the gas extraction system, and may compile the data into a record. FIG. 11 illustrates an example record of calibration measurements obtained by a landfill gas extraction system, in accordance with some embodiments of the technology described herein. The calibration record 1100 may be displayed to a user using a graphical user interface of the gas extraction system, as described herein.

The calibration record 1100 includes various blocks of information related to the calibration process. Block 1101 represents logistical information regarding a calibration cycle. For example, block 1101 displays data relating to the location of the calibration (e.g. system model, unit number, and well or header ID number), and the date and time of the calibration.

Block 1102 represents information related to calibration of one or more gas composition sensors. For example, block 1102 may indicate known concentrations for various gasses (e.g. $CH_4$, $CO_2$, $O_2$, $N_2$, etc.) in one or more calibration mediums (e.g. calibration fluid #1, calibration fluid #2). A batch ID identifying the source of the calibration fluid (i.e. an ID for the calibration bottle, ambient air, etc.) may be recorded in block 1102 as well. A reading of the one or more calibration fluids may be taken and recorded prior to calibration, and a subsequent reading of the one or more calibration fluid may be taken and recorded after calibration of the one or more sensors.

Block 1104 may record a determination as to whether the calibration of the one or more sensors is acceptable. For example, the accuracy of the confirmation reading measurements taken after calibration has been performed may determine whether the calibration has "passed" or "failed". In some embodiments, a calibration may be passing when the gas composition measurements obtained in the calibration reading are sufficiently close to the known gas composition values (e.g. within a threshold, such as within 1%, for example). In some embodiments, the calibration may be passing when the offset necessary for correcting sensor measurements is below a certain threshold (e.g., no more than 2%, no more than 5%, no more than 10%, etc.). An indication of "fail" may necessitate recalibrating the one or more sensors and/or repairing or replacing the one or more sensors of the gas extraction system. The gas extraction system may be configured to automatically notify a user when the calibration receives a failing report.

Similar information to that described herein with respect to the gas composition sensors at block 1102 may be presented with respect to temperature and pressure sensors. Block 1406 represents calibration information for a thermistor configured to sense temperature (e.g. of landfill gas, atmospheric temperature, calibration fluids, etc.). Block 1106 may display the date and time of a calibration, as well as temperature readings before and after a calibration is performed. Block 1106 may also include information related to the instrument used to calibrate the thermistor, including the make, model, and date of calibration. Block 1108 represents information related to the calibration of a pressure sensor, including the date, time, pressure measurements before and after calibration, and the medium used for calibration.

As described herein, the gas extraction system may include a graphical user interface (GUI) for displaying output of activity and settings of the gas extraction system and receiving input from a user. FIGS. 12-17 are examples of a graphical user interface configured for use with a landfill gas extraction system, in accordance with some embodiments of the technology described herein. In some embodiments, a separate GUI is provided for each of a plurality of landfills, and, in other embodiments, one or more GUIs can be configured to display data and receive input for multiple landfills. The GUI may be configured to display and receive data for multiple gas extraction systems at one or more landfills.

The GUI can be configured to receive data from and transmit data to a data store. For example, the GUI may be configured to receive input from a user that can be transmitted to a data store for storing the user input into memory. Similarly, the GUI can be configured to receive data from a data store such that the data stored in memory can be displayed using the GUI and viewed by a user. The GUI may be configured to compile data stored in memory in a format easily viewable by a user. For example, the GUI may be configured to display the calibration record 1100 based on data received from the data store. In some embodiments, the GUI may be configured to receive data directly from the gas extraction system, for example from the one or more sensors of the gas extraction system, and may display data without first receiving the data from a data store or storing the data into system memory.

FIGS. 12-17 illustrate various example display pages of a GUI configured for use with a gas extraction system. A user may be able to navigate through display pages of the GUI and otherwise provide input for the GUI using one or more input devices (e.g. a keyboard, mouse, and/or touch screen). The GUI may include a sidebar 1214 to facilitate navigation through the various display pages of the GUI, and an information panel 1210 to provide information about one or more landfills being monitored. For example, the information panel 1210 may provide information regarding the location of the landfill currently selected for display, as well as statistics regarding the activities of the landfill (e.g. number of active collectors, total $CH_4$ flow, total landfill gas flow, total $CO_2$, total $CH_4$, etc.). The sidebar 1214 may also provide an option for a user to toggle between different accounts or different landfills being monitored, by using a "Sign Out" button, for example.

Figure 12:
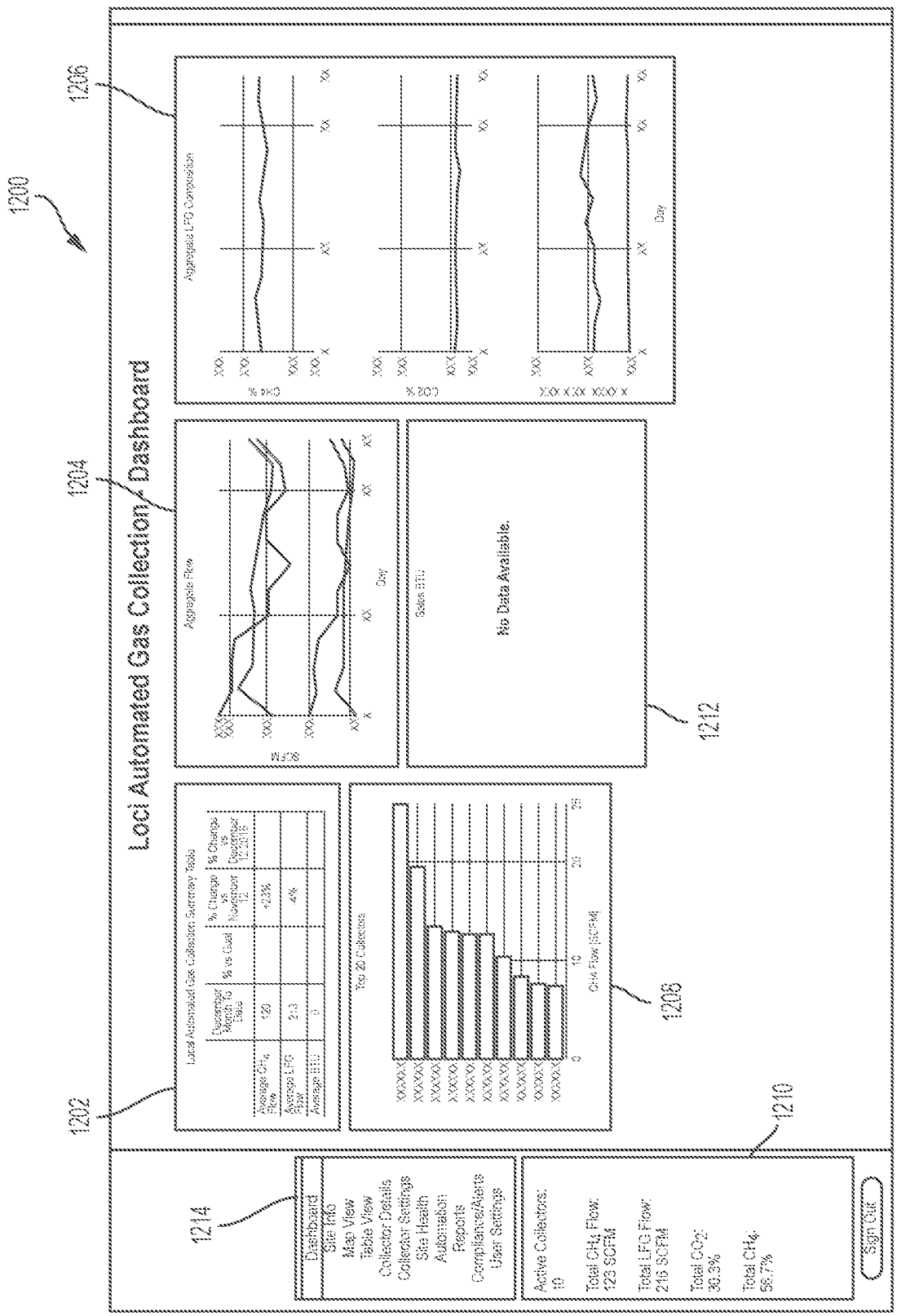

FIG. 12 illustrates a first example of a display page of a GUI configured for monitoring landfill gas extraction at one or more landfills, as described herein. In FIG. 12, a dashboard display page 1200 is displayed illustrating various graphics and other high-level information about one or more gas collection systems at a landfill. For example, block 1202 may illustrate a summary table of average landfill gas collection measurements. In the illustrated embodiment, block 1202 illustrates average $CH_4$ flow, average landfill gas flow, and average BTU in various percentages and over various time intervals. Blocks 1204 and 1206 illustrate graphics of aggregate flow and aggregate landfill gas composition for various constituent gasses, respectively. Block 1508 illustrates a table of the top twenty collection wells monitored by the GUI, in terms of total $CH_4$ flow or other selected parameters. Block 1212 illustrates total sales BTU for the landfill being monitored.

FIG. 13 illustrates another example of a display page of a GUI configured for monitoring landfill gas extraction at one or more landfills, as described herein. As shown in FIG. 13, display page 1300 illustrates various aspects of site health of a landfill gas extraction site. For example, display page 1300 displays a list of active alerts for the landfill gas extraction site. Column 1302 displays information relating to the type of alarm (e.g., a calibration error, communication loss, red flag alert, or yellow flag alert). Column 1304 displays information indicating which collector generated the alert, and column 1306 indicates a value of the alert (e.g., for a calibration error, column 1306 indicates the number of times a calibration process has "failed", as described herein). Display page 1300 may facilitate more efficient monitoring of a landfill gas extraction site and in turn, more expeditious correction of issues that arise.

In some embodiments, the alert generated by the gas extraction system and displayed on display page 1300 may depend on the severity of the issue detected. For example, FIG. 13 shows a "yellow flag" alert and a "red flag" alert for characteristics of the landfill gas extraction process. A yellow flag alert may be generated when a value for a selected characteristic exceeds or falls below a first threshold value for the selected characteristic. Corresponding corrective actions for a yellow flag alert may include preliminary actions, such as notifying a user. A red flag alert may be generated when a value for a selected characteristic exceeds or falls below a second threshold value for the selected characteristic. Corresponding corrective actions for a red flag alert may be more severe, such as adjusting a flow control mechanism of the gas extraction system. Methods of notifying a user of a yellow flag alert and a red flag alert may differ. For example, a yellow flag alert may generate an email and/or a push notification, which a red flag alert may generate a phone call, text message and/or an alarm. Any of the methods described herein may be modified by implementing first and second threshold values for generating yellow flag and red flag alerts.

Figure 14:
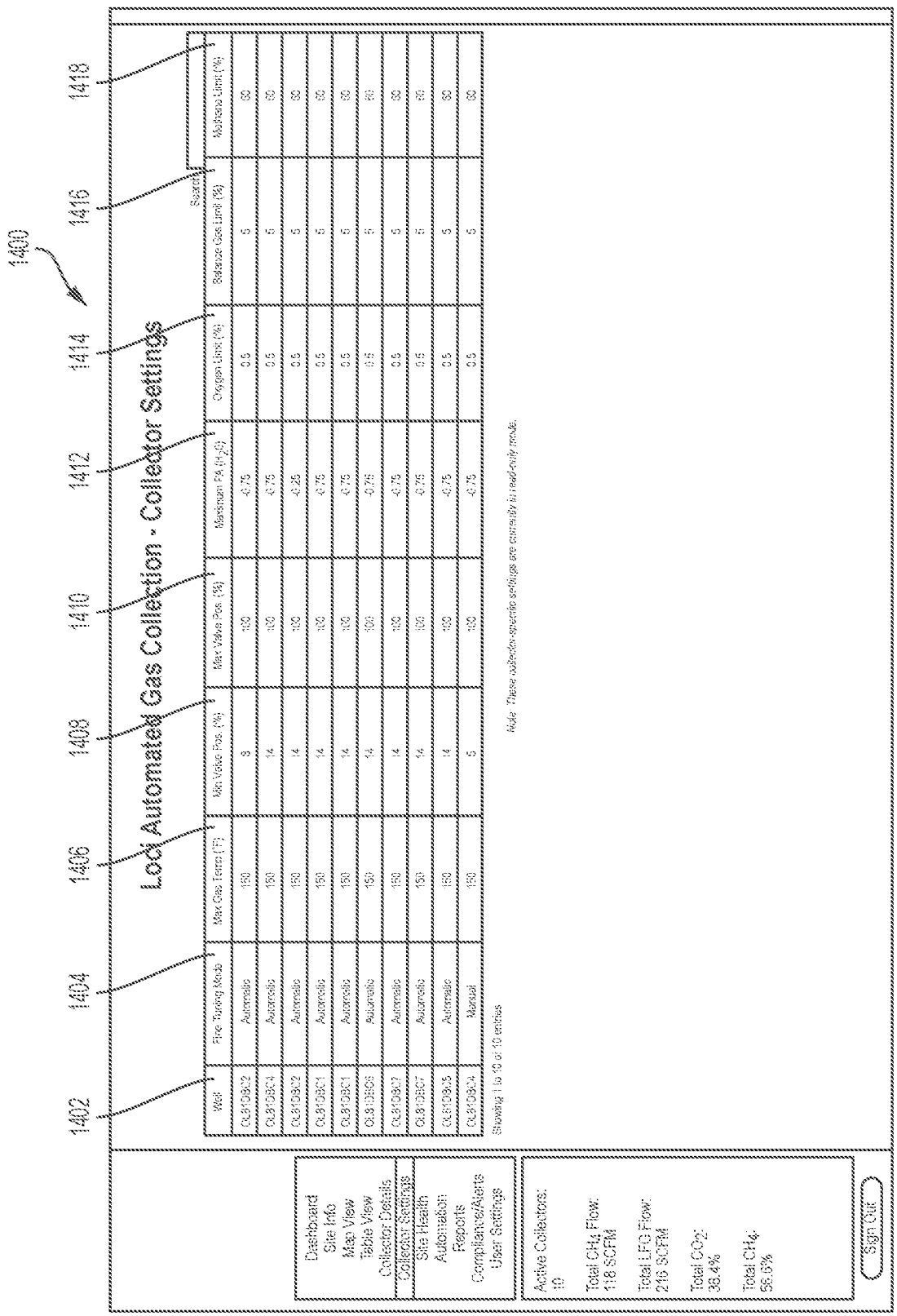

FIG. 14 illustrates another example of a display page of a GUI configured for monitoring landfill gas extraction at one or more landfills, as described herein. FIG. 14 shows a display page 1400 indicating the current settings applicable to a plurality of wells at the landfill gas extraction site. For example, column 1402 indicates a well identifier indicating the well that the settings shown on display page 1400 apply to. The settings displayed on display page 1400 may include, a tuning mode 1404, maximum gas temperature 1406, minimum valve position 1408, maximum valve position 1410, maximum pressure 1412, oxygen limit 1414, balance gas limit 1416, and methane limit 1418, for example. The tuning mode 1404 may indicate whether adjustments to the flow rate of extracted landfill gas for the purposes of compliance, methane optimization, and/or other reasons, are made manually, or automatically using the processes described herein. The settings shown on display page 1400 may be predefined or, in some embodiments, may be input by a user, for example, using the GUI, as described herein, for example, with respect to FIGS. 15-16.

Figure 15:
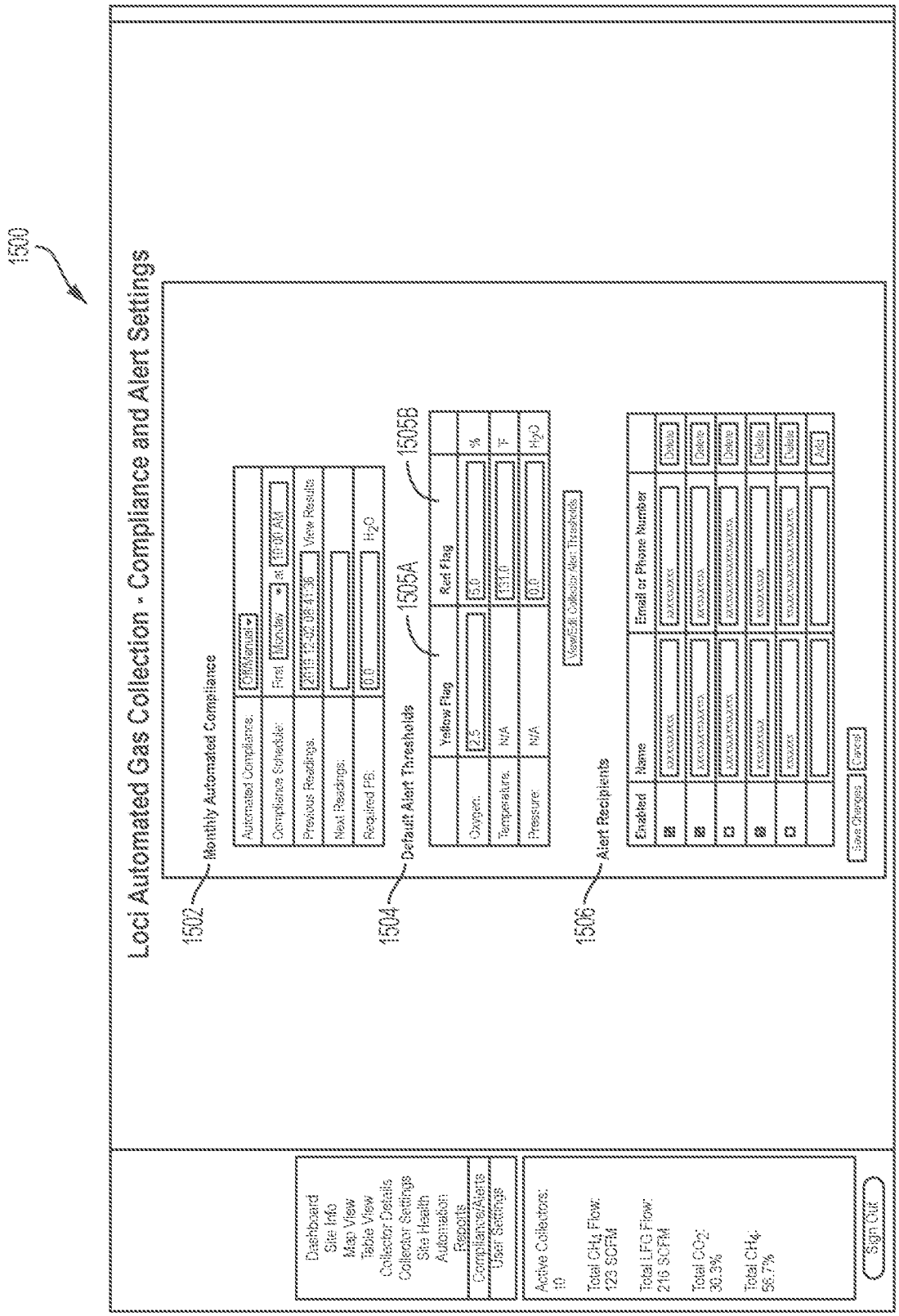

FIG. 15 illustrates another example of a display page of a GUI configured for monitoring landfill gas extraction at one or more landfills, as described herein. As shown in FIG. 15, display page 1500 includes fields configured to receive user input regarding a number of settings to be applied to the landfill gas extraction site. For example, block 1502 includes user definable settings for performing automated compliance methods, for example, the methods described herein. At block 1502, a user can define whether to perform automated compliance and the time at which automated compliance processes should be performed. Block 1502 may also display information indicating the dates of the previous compliance reading and the next compliance reading, with an option to view the results of the previous compliance reading.

At block 1504, a user can define default alert thresholds, including default thresholds for yellow flag 1505A and red flag 1505B alerts for selected characteristics of the landfill gas extraction process. For example, in the illustrated embodiment, block 1804 allows a user to define default alert thresholds for oxygen, temperature, and pressure.

At block 1506, a user can define alert recipients, including the name and contact information of the alert recipient. A user may be able to store alert recipients in the GUI and toggle alerts on/off for that recipient. Block 1506 may also allow a user to choose how an alert recipient should be contacted (e.g. email, phone, or both).

Figure 16:
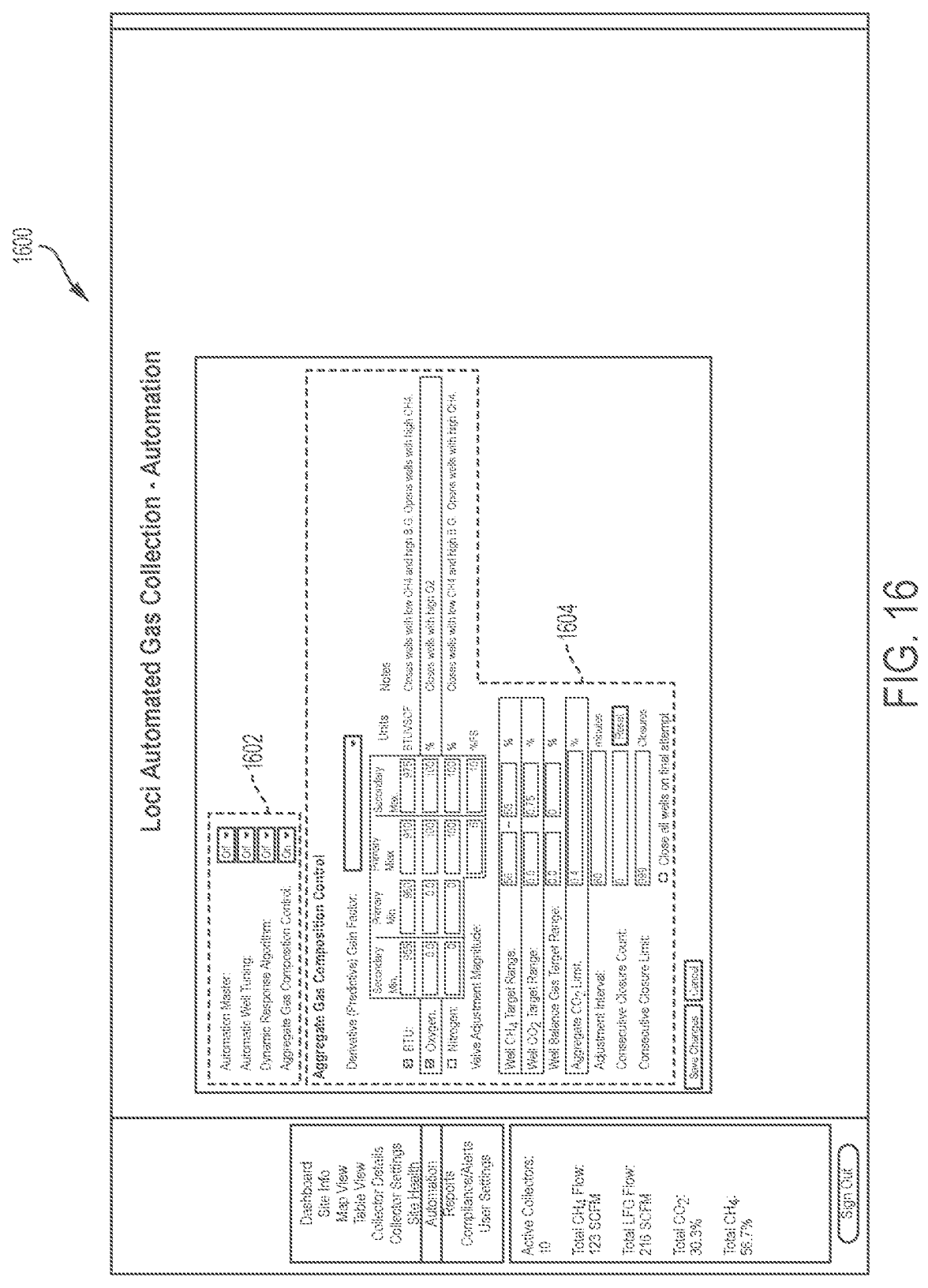

FIG. 16 illustrates another example of a display page of a GUI configured for monitoring landfill gas extraction at one or more landfills, as described herein. As shown in FIG. 16, display page 1600 includes additional fields configured to receive user input regarding a number of settings to be applied to the landfill gas extraction site. For example, block 1602 provides various automation processes application to landfill gas extraction that can be toggled on/off. Block 1604 further provides user definable settings for target gas composition parameters and process controls (e.g., increments to adjust a valve of a flow control mechanism). In some embodiments, the user definable parameters may include preliminary and secondary minimum and maximum values, such that landfill gas extraction can be performed according to multiple sets of parameters.

FIG. 17 illustrates another example of a display page of a GUI configured for monitoring landfill gas extraction at one or more landfills, as described herein. As shown in FIG. 17, a display page 1700 is provided for displaying current measurements of a landfill gas extraction site. Column 1702 may indicate a well identifier indicating the well that the measurements shown on display page 1700 were obtained from. Columns 1704 include a number of values for characteristics of the gas extraction process, including, for example, $CH_4$ concentration, $O_2$ concentration, $CO_2$ concentration, balance gas concentration, landfill gas flow rate, temperature, pressure, and valve position.

Systems and methods for automatically monitoring and controlling a landfill gas extraction system to ensure safe landfill gas extraction while optimizing the quality of extracted landfill gas and providing for automatic compliance with regulations governing landfill gas extraction have been described herein. In some embodiments, the methods described herein are implemented by one or more components of a system being coupled to at least one sensor and at least one flow control mechanism of a gas extraction system, for example, by at least one controller of the system, while in other embodiments, the methods may be partially or completely implemented by an external device.

In some embodiments, performing a corrective action may include decreasing a flow rate of the extracted landfill gas. In some embodiments, decreasing a flow rate of the extracted landfill gas may include stopping flow of the extracted landfill gas, however, preferably decreasing flow rate of extracted landfill gas does not include stopping flow of the extracted landfill gas as the inventors have recognized that stopping all flow of the gas extraction system may cause additional dangerous conditions for the landfill site.

Figure 18:
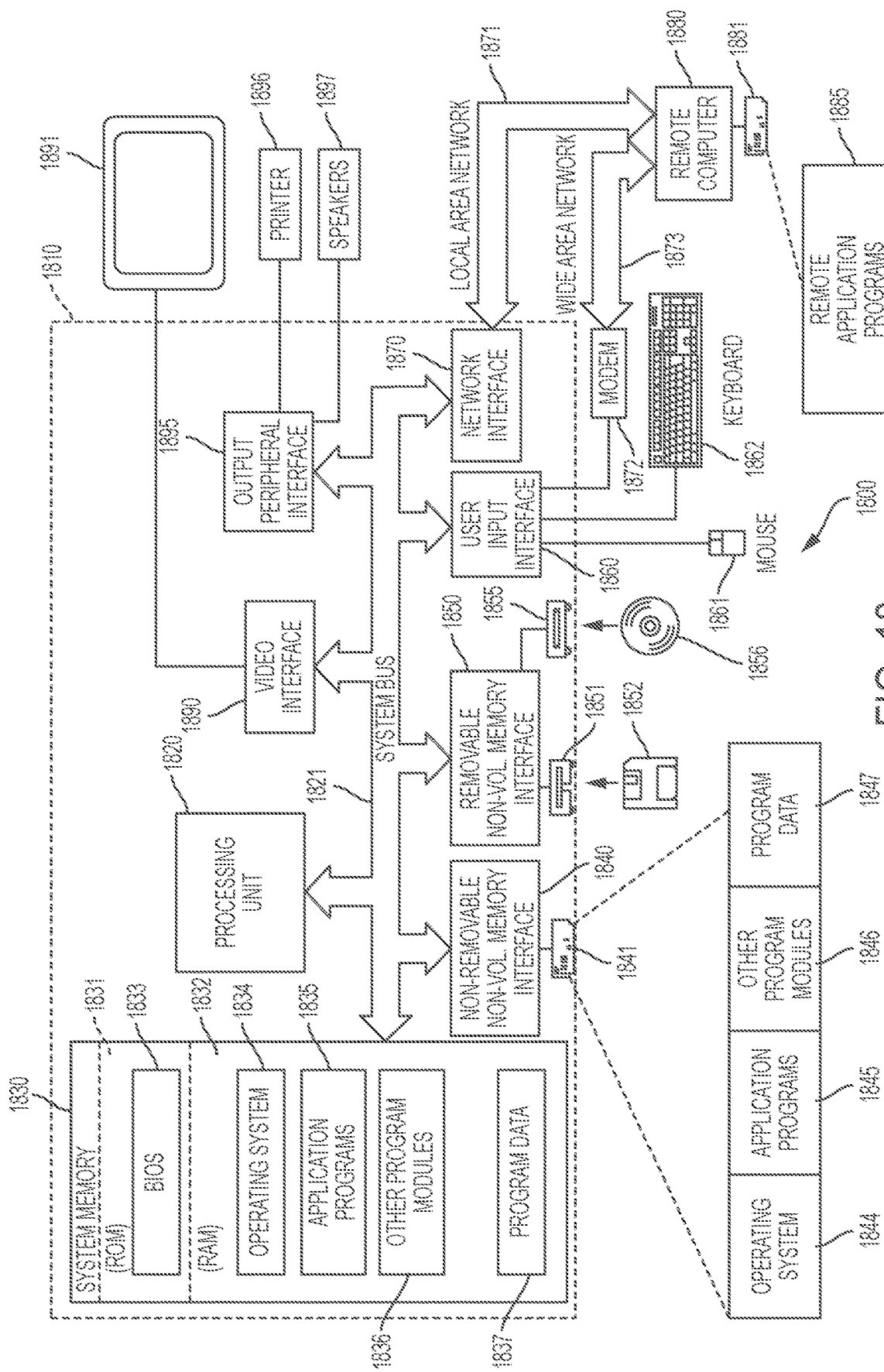
FIG. 18 is a block diagram of an example computer system in which aspects of the present disclosure may be implemented, according to some embodiments of the technology described herein.

FIG. 18 is a block diagram of an example computer system in which aspects of the present disclosure may be implemented, according to some embodiments of the technology described herein. In some embodiments, portions of a landfill gas extraction control system may be implemented in a computing system environment. For example, in some embodiments, Device Manager 902, Controller Module 904, User Interface 908, and/or Database 910 may be implemented in a computing system environment. In some embodiments, aspects of one or more techniques describes herein may be implemented in a computing system environment.

The computing system environment 1800 is only one example of a suitable computing environment and is not intended to suggest any limitation as to the scope of use or functionality of the devices and techniques disclosed herein. Neither should the computing environment 1800 be interpreted as having any dependency or requirement relating to any one or combination of components illustrated in the exemplary operating environment 1800.

The techniques disclosed herein are operational with numerous other general purpose or special purpose computing system environments or configurations. Examples of well-known computing systems, environments, and/or configurations that may be suitable for use with techniques disclosed herein include, but are not limited to, personal computers, server computers, hand-held devices (e.g., smart phones, tablet computers, or mobile phones), laptop devices, multiprocessor systems, microprocessor-based systems, set top boxes, programmable consumer electronics, network PCs, minicomputers, mainframe computers, distributed computing environments that include any of the above systems or devices, and the like.

The computing environment may execute computer-executable instructions, such as program modules. Generally, program modules include routines, programs, objects, components, data structures, etc. that perform particular tasks or implement particular abstract data types. The technology described herein may also be practiced in distributed computing environments where tasks are performed by remote processing devices that are linked through a communications network. In a distributed computing environment, program modules may be located in both local and remote computer storage media including memory storage devices.

With reference to FIG. 18, an exemplary system for implementing techniques described herein includes a general purpose computing device in the form of a computer 1810. Components of computer 1810 may include, but are not limited to, a processing unit 1820, a system memory 1830, and a system bus 1821 that couples various system components including the system memory to the processing unit 1820. The system bus 1821 may be any of several types of bus structures including a memory bus or memory controller, a peripheral bus, and/or a local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus also known as Mezzanine bus.

Computer 1810 typically includes a variety of computer readable media. Computer readable media can be any available media that can be accessed by computer 1810 and includes both volatile and nonvolatile media, removable and non-removable media. By way of example, and not limitation, computer readable media may comprise computer storage media and communication media. Computer storage media includes both volatile and nonvolatile, removable and non-removable media implemented in any method or technology for storage of information such as computer readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can accessed by computer 1810. Communication media typically embodies computer readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of the any of the above should also be included within the scope of computer readable media.

The system memory 1830 includes computer storage media in the form of volatile and/or nonvolatile memory such as read only memory (ROM) 1831 and random access memory (RAM) 1832. A basic input/output system 1833 (BIOS), containing the basic routines that help to transfer information between elements within computer 1810, such as during start-up, is typically stored in ROM 1831. RAM 1832 typically contains data and/or program modules that are immediately accessible to and/or presently being operated on by processing unit 1820. By way of example, and not limitation, FIG. 18 illustrates operating system 1834, application programs 1835, other program modules 1836, and program data 1837.

The computer 1810 may also include other removable/non-removable, volatile/nonvolatile computer storage media. By way of example only, FIG. 18 illustrates a hard disk drive 1841 that reads from or writes to non-removable, nonvolatile magnetic media, a magnetic disk drive 1851 that reads from or writes to a removable, nonvolatile magnetic disk 1852, and an optical disk drive 1855 that reads from or writes to a removable, nonvolatile optical disk 1856 such as a CD ROM or other optical media. Other removable/non-removable, volatile/nonvolatile computer storage media that can be used in the exemplary operating environment include, but are not limited to, magnetic tape cassettes, flash memory cards, digital versatile disks, digital video tape, solid state RAM, solid state ROM, and the like. The hard disk drive 1841 is typically connected to the system bus 1821 through an non-removable memory interface such as interface 1840, and magnetic disk drive 1851 and optical disk drive 1855 are typically connected to the system bus 1821 by a removable memory interface, such as interface 1850.

The drives and their associated computer storage media described above and illustrated in FIG. 18, provide storage of computer readable instructions, data structures, program modules and other data for the computer 1810. In FIG. 18, for example, hard disk drive 1841 is illustrated as storing operating system 1844, application programs 1845, other program modules 1846, and program data 1847. Note that these components can either be the same as or different from operating system 1834, application programs 1835, other program modules 1836, and program data 1837. Operating system 1844, application programs 1845, other program modules 1846, and program data 1847 are given different numbers here to illustrate that, at a minimum, they are different copies. A user may enter commands and information into the computer 1810 through input devices such as a keyboard 1862 and pointing device 1861, commonly referred to as a mouse, trackball or touch pad. Other input devices (not shown) may include a microphone, joystick, game pad, satellite dish, scanner, or the like. These and other input devices are often connected to the processing unit 1820 through a user input interface 1860 that is coupled to the system bus, but may be connected by other interface and bus structures, such as a parallel port, game port or a universal serial bus (USB). A monitor 1891 or other type of display device is also connected to the system bus 1821 via an interface, such as a video interface 1890. In addition to the monitor, computers may also include other peripheral output devices such as speakers 1897 and printer 1896, which may be connected through a output peripheral interface 1895.

The computer 1810 may operate in a networked environment using logical connections to one or more remote computers, such as a remote computer 1880. The remote computer 1880 may be a personal computer, a server, a router, a network PC, a peer device or other common network node, and typically includes many or all of the elements described above relative to the computer 1810, although only a memory storage device 1881 has been illustrated in FIG. 18. The logical connections depicted in FIG. 18 include a local area network (LAN) 1871 and a wide area network (WAN) 1873, but may also include other networks. Such networking environments are commonplace in offices, enterprise-wide computer networks, intranets and the Internet.

When used in a LAN networking environment, the computer 1810 is connected to the LAN 1871 through a network interface or adapter 1870. When used in a WAN networking environment, the computer 1810 typically includes a modem 1872 or other means for establishing communications over the WAN 1873, such as the Internet. The modem 1872, which may be internal or external, may be connected to the system bus 1821 via the user input interface 1860, or other appropriate mechanism. In a networked environment, program modules depicted relative to the computer 1810, or portions thereof, may be stored in the remote memory storage device. By way of example, and not limitation, FIG. 18 illustrates remote application programs 1885 as residing on memory device 1881. It will be appreciated that the network connections shown are exemplary and other means of establishing a communications link between the computers may be used.

Embodiments of the above-described techniques can be implemented in any of numerous ways. For example, the embodiments may be implemented using hardware, software or a combination thereof. When implemented in software, the software code can be executed on any suitable processor or collection of processors, whether provided in a single computer or distributed among multiple computers. In some embodiments, at least some (e.g., all) of the functions performed by an In Situ Control Mechanism 106 and/or a Controller 304 may be implemented as software executed on one or more processors.

Such processors may be implemented as integrated circuits, with one or more processors in an integrated circuit component, including commercially available integrated circuit components known in the art by names such as CPU chips, GPU chips, microprocessor, microcontroller, or co-processor. Alternatively, a processor may be implemented in custom circuitry, such as an ASIC, or semicustom circuitry resulting from configuring a programmable logic device. As yet a further alternative, a processor may be a portion of a larger circuit or semiconductor device, whether commercially available, semi-custom or custom. As a specific example, some commercially available microprocessors have multiple cores such that one or a subset of those cores may constitute a processor. Though, a processor may be implemented using circuitry in any suitable format.

Further, it should be appreciated that a computer may be embodied in any of a number of forms, such as a rack-mounted computer, a desktop computer, a laptop computer, or a tablet computer. Additionally, a computer may be embedded in a device not generally regarded as a computer but with suitable processing capabilities, including a Personal Digital Assistant (PDA), a smart phone or any other suitable portable or fixed electronic device.

Also, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computer may receive input information through speech recognition or in other audible format.

Such computers may be interconnected by one or more networks in any suitable form, including as a local area network or a wide area network, such as an enterprise network or the Internet. Such networks may be based on any suitable technology and may operate according to any suitable protocol and may include wireless networks, wired networks or fiber optic networks.

Also, the various methods or processes outlined herein may be coded as software that is executable on one or more processors that employ any one of a variety of operating systems or platforms. Additionally, such software may be written using any of a number of suitable programming languages and/or programming or scripting tools, and also may be compiled as executable machine language code or intermediate code that is executed on a framework or virtual machine.

In this respect, the technology described herein may be embodied as a computer readable storage medium (or multiple computer readable media) (e.g., a computer memory, one or more floppy discs, compact discs (CD), optical discs, digital video disks (DVD), magnetic tapes, flash memories, circuit configurations in Field Programmable Gate Arrays or other semiconductor devices, or other tangible computer storage medium) encoded with one or more programs that, when executed on one or more computers or other processors, perform methods that implement the various embodiments of the technology described herein. As is apparent from the foregoing examples, a computer readable storage medium may retain information for a sufficient time to provide computer-executable instructions in a non-transitory form. Such a computer readable storage medium or media can be transportable, such that the program or programs stored thereon can be loaded onto one or more different computers or other processors to implement various aspects of the technology described herein. As used herein, the term "computer-readable storage medium" encompasses only a computer-readable medium that can be considered to be a manufacture (i.e., article of manufacture) or a machine. Alternatively or additionally, the technology described herein may be embodied as a computer readable medium other than a computer-readable storage medium, such as a propagating signal.

The terms "program" or "software" are used herein in a generic sense to refer to any type of computer code or set of computer-executable instructions that can be employed to program a computer or other processor to implement various aspects of the technology described herein as described above. Additionally, it should be appreciated that according to one aspect of this embodiment, one or more computer programs that when executed perform methods of the technology described herein need not reside on a single computer or processor, but may be distributed in a modular fashion amongst a number of different computers or processors to implement various aspects of the technology described herein.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that conveys relationship between the fields. However, any suitable mechanism may be used to establish a relationship between information in fields of a data structure, including through the use of pointers, tags or other mechanisms that establish relationship between data elements.

Various aspects of the technology described herein may be used alone, in combination, or in a variety of arrangements not specifically described in the embodiments described in the foregoing and is therefore not limited in its application to the details and arrangement of components set forth in the foregoing description or illustrated in the drawings. For example, aspects described in one embodiment may be combined in any manner with aspects described in other embodiments.

Also, the technology described herein may be embodied as a method, of which an example has been provided, including FIGS. 4-7 and their accompanying descriptions. The acts performed as part of the method may be ordered in any suitable way. Accordingly, embodiments may be constructed in which acts are performed in an order different than illustrated, which may include performing some acts simultaneously or concurrently, even though shown as sequential acts in illustrative embodiments.

Various events/acts are described herein as occurring or being performed at a specified time. One of ordinary skill in the art would understand that such events/acts may occur or be performed at approximately the specified time.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

The terms "substantially", "approximately", and "about" may be used to mean within ±20% of a target value in some embodiments, within ±10% of a target value in some embodiments, within ±5% of a target value in some embodiments, within ±2% of a target value in some embodiments. The terms "approximately" and "about" may include the target value.

Having thus described several aspects of at least one embodiment of the technology described herein, it is to be appreciated that various alterations, modifications, and improvements will readily occur to those skilled in the art. Such alterations, modifications, and improvements are intended to be part of this disclosure, and are intended to be within the spirit and scope of the present disclosure. Further, though advantages of some embodiments of the technology described herein are indicated, it should be appreciated that not every embodiment will include every described advantage. Some embodiments may not implement any features described as advantageous herein and in some instances. Accordingly, the foregoing description and drawings are by way of example only.

What is claimed is:

1. A method for use by a system coupled to at least one sensor and at least one flow control mechanism of a gas extraction system, the system comprising at least one controller and being configured for use in connection with a landfill gas extraction process for extraction of landfill gas from a landfill via the gas extraction system, the method comprising:
using the at least one controller of the system to perform:
obtaining, based on at least one measurement made by the at least one sensor, a first measure of pressure in the gas extraction system;
determining, based on the first measure of pressure in the gas extraction system, whether pressure in the gas extraction system is negative;
when it is determined that the pressure in the gas extraction system is not negative, increasing a flow rate of landfill gas being extracted from the landfill via the gas extraction system;
subsequent to increasing the flow rate of landfill gas being extracted from the landfill and after a first amount of time has passed since the obtaining the first measure of pressure in the gas extraction system, obtaining a second measure of pressure in the gas extraction system; and
in response to determining that the second measure of pressure in the gas extraction system is not negative and if the first amount of time is greater than or equal to a threshold amount of time, performing a second corrective action other than increasing the flow rate of the landfill gas being extracted from the landfill via the gas extraction system.

2. The method of claim 1, further comprising:
subsequent to increasing the flow rate, obtaining a value of oxygen concentration of landfill gas extracted from the landfill; and
determining whether the value of oxygen concentration complies with a compliance criterion for oxygen concentration.

3. The method of claim 1, further comprising:
subsequent to increasing the flow rate, obtaining a value of gas temperature of landfill gas extracted from the landfill; and
determining whether the value of gas temperature complies with a compliance criterion for gas temperature.

4. The method of claim 1, further comprising, in response to determining that the pressure in the gas extraction system is not negative, generating an alert.

5. The method of claim 1, wherein the at least one controller is configured to determine whether the pressure in the gas extraction system is negative at least once per month.

6. The method of claim 1, wherein the at least one sensor is disposed in well piping of the gas extraction system below the at least one flow control mechanism.

7. The method of claim 1, further comprising in response to determining that the second measure of pressure in the gas extraction system is negative, storing the first amount of time in a database.

8. A system coupled to at least one sensor and at least one flow control mechanism of a gas extraction system, the system being configured for use in connection with a landfill gas extraction process for extraction of landfill gas from a landfill via the gas extraction system, the system comprising:
  at least one controller configured to:
    obtain, based on at least one measurement made by the at least one sensor, a first measure of pressure in the gas extraction system;
    determine, based on the first measure of pressure in the gas extraction system, whether pressure in the gas extraction system is negative;
    when it is determined that the pressure in the gas extraction system is not negative, increase a flow rate of landfill gas being extracted from the landfill via the gas extraction system;
    subsequent to increasing the flow rate of landfill gas being extracted from the landfill and after a first amount of time has passed since obtaining the first measure of pressure in the gas extraction system, obtaining a second measure of pressure in the gas extraction system; and
    in response to determining that the second measure of pressure in the gas extraction system is not negative and if the first amount of time is greater than or equal to a threshold amount of time, performing a second corrective action other than increasing the flow rate of the landfill gas being extracted from the landfill via the gas extraction system.

9. The system of claim 8, wherein the at least one controller is further configured to:
  subsequent to increasing the flow rate, obtain a value of oxygen concentration of landfill gas extracted from the landfill; and
  determine whether the value of oxygen concentration complies with a compliance criterion for oxygen concentration.

10. The system of claim 8, wherein the at least one controller is further configured to:
  subsequent to increasing the flow rate, obtain a value of gas temperature of landfill gas extracted from the landfill; and
  determine whether the value of gas temperature complies with a compliance criterion for gas temperature.

11. The system of claim 8, wherein the at least one controller is further configured to generate an electronic alert when it is determined that the pressure in the gas extraction system is not negative.

12. The system of claim 8, wherein the at least one controller is configured to determine whether the pressure in the gas extraction system is negative at least once per month.

13. The system of claim 8, wherein the at least one sensor is disposed in well piping of the gas extraction system below the at least one flow control mechanism.

14. The system of claim 8, wherein the at least one controller is further configured to, in response to determining that the second measure of pressure in the gas extraction system is negative, store the first amount of time in a database.

\* \* \* \* \*